US007452866B2

(12) United States Patent
Thorn et al.

(10) Patent No.: US 7,452,866 B2
(45) Date of Patent: Nov. 18, 2008

(54) METHODS OF INHIBITING ANGIOGENESIS WITH FRAGMENTS AND HOMOLOGS OF TROPONIN SUBUNIT 1

(75) Inventors: Richard M. Thorn, North Easton, MA (US); Mark A. Lanser, Dover, MA (US); Marsha A. Moses, Brookline, MA (US); Dmitri G. Wiederschain, Brighton, MA (US)

(73) Assignees: Children's Medical Center Corporation, Boston, MA (US); Alseres Pharmaceuticals, Inc., Hopkinton, MA (US)

( * ) Notice: Subject to any disclaimer, the term of this patent is extended or adjusted under 35 U.S.C. 154(b) by 305 days.

(21) Appl. No.: 11/327,174

(22) Filed: Jan. 5, 2006

(65) Prior Publication Data

US 2006/0211614 A1    Sep. 21, 2006

Related U.S. Application Data

(63) Continuation of application No. 10/176,416, filed on Jun. 18, 2002, now Pat. No. 7,078,385, which is a continuation of application No. 09/442,099, filed on Nov. 17, 1999, now Pat. No. 6,465,431, which is a continuation-in-part of application No. 09/268,274, filed on Mar. 15, 1999, now abandoned, which is a continuation-in-part of application No. 08/961,264, filed on Oct. 30, 1997, now Pat. No. 6,025,331, which is a continuation of application No. 08/602,941, filed on Feb. 16, 1996, now Pat. No. 5,837,680.

(51) Int. Cl.
*A61K 38/16* (2006.01)
*C07K 14/00* (2006.01)

(52) U.S. Cl. .................. 514/12; 514/2; 530/324

(58) Field of Classification Search .................. 514/12; 530/324
See application file for complete search history.

(56) References Cited

U.S. PATENT DOCUMENTS

| 5,583,200 A | 12/1996 | Larue et al. |
| 5,837,680 A | 11/1998 | Moses et al. |
| 6,025,331 A | 2/2000 | Moses et al. |

FOREIGN PATENT DOCUMENTS

| GB | 2 275774 A | 9/1994 |
| WO | WO 97 30085 | 8/1997 |

OTHER PUBLICATIONS

Altschul et al., 1990, "Basic local alignment search tool", J Mol Biol 215:403-410.
Altschul et al., 1997 "Gapped BLAST and PSI-BLAST: a new generation of protein database search programs", Nuc Acids Res 25:3389-3402.
Auerbach et al., 1985, "Expression of organ-specific antigens on capillary endothelial cells", Microvasc Res 29:401-411.
Baldwin, Jr., et al., 1985, "Structure, evolution and regulation of a fast skeletal troooponin I gene", Proc. Natl. Acad. Sci. USA, 82:8080-8084.
Blood and Zetter, 1990, "Tumor interactions with the vasculature: angiogenesis and tumor metastasis", Biochem Biophys Acta 1032:89-118.
Boyden et al., 1962, "The chemotactic effect of mixtures of antibody and antigen on polymorphonuclear leucocytes", J. Exp. Med. 115: 453-466.
Brekke and Greaser, 1976, "Separation and characterization of the troponin components from bovine cardiac muscle", J Biol Chem 251:886-871.
Chen et al., 1988, FEBS Lett. 228:22-26.
Chen et al., 1995, "A strategy to discover circulating angiogenesis inhibitors generated by human tumors", Cancer Res 55:4230-4233.
D'Amore, 1986, "Growth factors, angiogenesis and metastasis", Prog Clin Biol Res 221:269-283.
D'Amore and Smith, 1993, "Growth factor effects on cells of the vascular wall: a survey", Growth Factors 8:61-75.
Ebashi et al., 1968, "Troponin: Preparation and physiological function", J Biochem 64:465.
Fal k et al., 1980, "A 48-well micro chemotaxis assembly for rapid and accurate measurement of leukocyte migration", J Immunol Methods 33:239-247.
Folkman, 1985, "Tumor angiogenesis", in *Advances in Cancer Research*, vol. 43, Klein and Weinhouse (eds.), Academic Press, NY, pp. 175-203.
Folkman et al., 1983, "Angiogenesis inhibition and tumor regression caused by heparin or a heparin fragment in the presence of cortisone", Science 221:719-725.
Folkman and Klagsbrun, 1987, "Angiogenic factors", Scieice 235:442-447.
Folkman et al., 1989, "Control of angiogenesis with synthetic heparin substitutes", Science 243:1490-1493.
Folkman, 1995, "Clinical applications of research on angiogenesis", New Eng J Med 333:1757-1763.
Gahlmann et al., 1988, J. Mol. Biol. 201:379-391.
Gahlmann and Kedes, 1990, "Cloning, structural analysis, and expression of the human fast twitch skkeletal muscle troponin C gene", J Biol Chem 265:12520-12528.
Garabarek and Drabikowski, 1981, "Proteolytic fragments of troponin C: Interactions with the other troponin subunits and biological activity", J Biol Chem 256:13121-13127.
Gartner and Henkind, 1978, "Neovascularization of the iris (*Rubeosis iridis*)", Surv. Ophthalmol. 22: 291-312.

(Continued)

*Primary Examiner*—Michael Borin
(74) *Attorney, Agent, or Firm*—Nixon Peabody LLP

(57) ABSTRACT

The present invention relates to methods of inhibiting angiogenesis associated with a disease or disorder with peptides homologous to amino acid residues 130-137 or 132-139 of human troponin subunit I.

17 Claims, 15 Drawing Sheets

OTHER PUBLICATIONS

Figure 1:
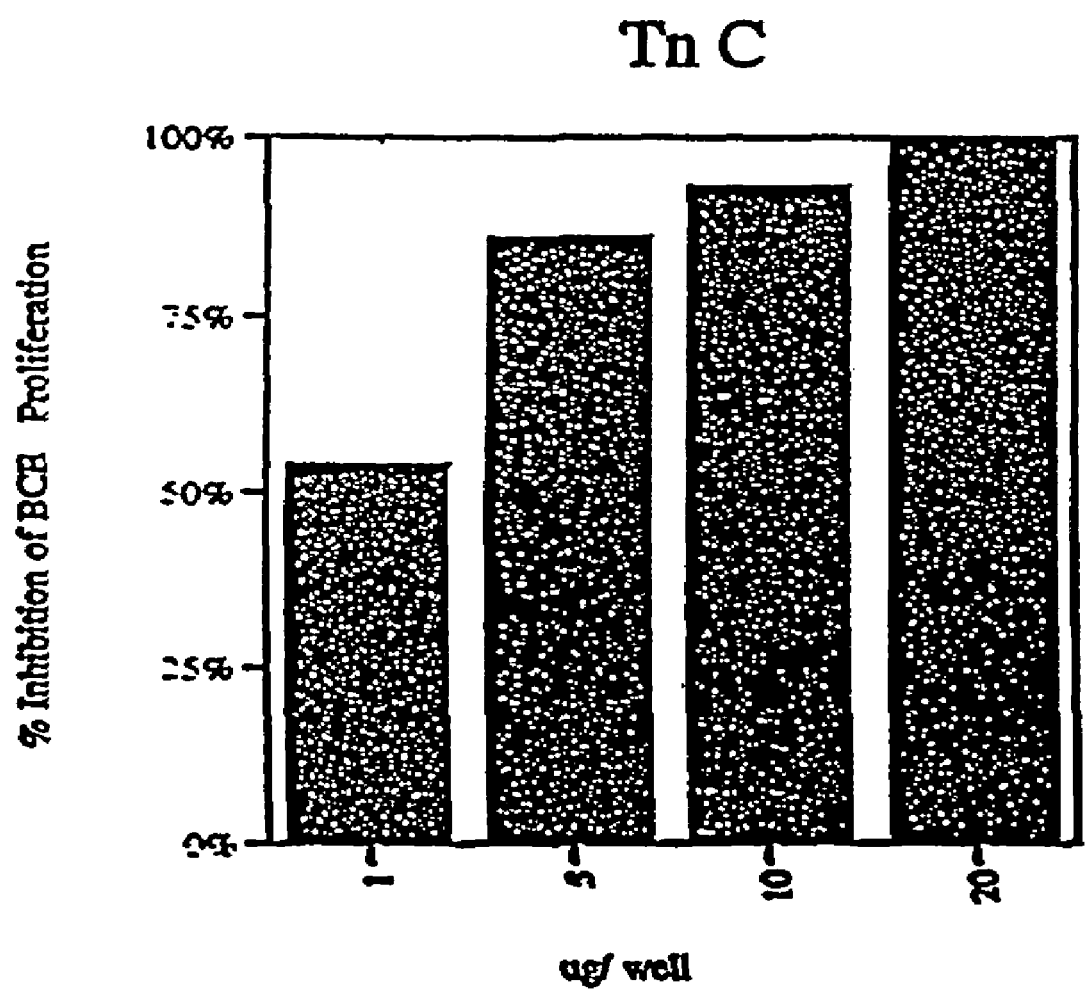

Gerson, S.L., 1999, Nature Med. 5: 262-264.
Glaser and D'Amore, 1980, "Adult tissues contain chemo-attractants for vascular endothelial cells", Nature 288:483-484.
Greaser and Gergely, 1971, "Reconstitution of troponin activity from three proteins components", J Biol Chem 246:4226-4233.
Greaser and Gergely, 1973, "Purification and properties of the components from tropinin", J Biol Chem 248:2125-2133.
Hartshorne and Mueller, 1968, "Fractionation of troponin into two distinct proteins", Biochem Biophys Res Comm 31:647-653.
Haudenschild et al., 1976, "Human vascular endothelial cells in culture. Lack of response to serum growth factors", Exp. Cell. Res. 98: 175-183.
Hartshorne and Mueller, 1969, "The preparation of tropomyosin and troponin frm natural actomyosin", Biochim Biophys Acta 175:301-319.
Higgins et al., 1996, "Using CLUSTAL for multiple sequence alignments", Methods Enzymol 266:383-402.
Hodges et al.., 1988, "computer simulation of high-performance liquid chromatographic separations of peptide and protein digests for development of size-exclusion, ion-exchange and reversed-phase chromatographic methods", J Chromatogr. 458:147-167.
Howard et al., 1989, "Intracerebral drug delivery in rats with lesion-induced memory deficits", J Neurogurg 71:105-112.
Jha et al., 1996, "Photo-cross-linking of rabbit skeletal troponin I deletion mutants with troponin C and its thoil mutants: The inhibitory region enchances binding of troponin I fragments to troponin C", Biochem 35:11026-11035.
Klagsbrun et al., 1977, "The stimulation of DNA synthesis and cell division in chondrocytes and 3T3 cells by a growth factor isolated from cartilage", Exp Cell Res 105:99-108.
Klagsbrun et al., 1991, "Regulators of angiogenesis", Annu Rev Physiol 53:217-239.
Kohn et al., 1997, Clin. Exp. Immunol. 107: 54-57.
Langer and Folkman, 1976, "Polymers for the sustained release of proteins and other macromolecules", Nature 263:797-800.
Langer et al., 1976, "Isolation of a cartilage factor that inhibits tumor neovascularization", Science 193:70-72.
Langer and Peppas, 1983, "Chemical and physical structure of polymers as carriers for controlled release of bioactive agents: a review", J Macromol Sci Rev Macromol Chem Phys 23:61-126.
Langer, 1990, "New methods of drug delivery", Science 249:1527-1533.
Levy et al., 1985, "Inhibition of calcification of bioprosthetic heart valves by local controlled-release diphosphonate", Science 228:190-192.
Lutty et al., 1983, "Vitreous: An inhibitor of retinal extract-induced neovascularization", Invest Ophthalmol Vis Sci 24:52-56.
Mant et al., "Separation of peptides by strong cation-exchange high-performance liquid chromatography", J Chromatogr., 327: 147-155.
Morris and Lehrer, 1984, "Troponin-tropomyosin interactions. Fluorescence studies of the binding of troponin, troponin T and chimotryptic troponin T fragments to specifically labeled tropomyosin", Biochem 23:2214-2220.
Moses et al., 1990, "Identification of an inhibitor of neovascularization from cartilage", Science 248:1408-1410.
Moses et al., 1992, "Isolation and characterization of an inhibitor of neovascularization from scapular chondrocytes", J Cell Biol 119:475-482.
Moses and Langer, 1991, "Inhibitors of angiogenesis", Biotechnology 9:630-634.
Moses et al., 1995, "The role of growth factors in vascular cell development and differentiation", Intl Rev Cytology, 161:1-48.
Moses et al., 1999, Troponin I is present in human cartilage and inhibits angiogenesis, Proc Natl Acad Sci USA 96:2645-2650.
Nash et al., 1996, "Cloning of a yeast 8-oxoguanine DNA glycosylase reveals the existence of a base-excision DNA-repair protein superfamily" Curr Biol 6:968-980.
Nikovits et al., 1986, "The chicken fast skeletal troponin I gene: exon organization and sequence", Nucleic Acids. Res., 14:3377-3390.
O'Reilly et al., 1996, "Angiostatin induces and sustains dormancy of human primary tumors in mice", Nat Med 2:689-692.

Patz et al., 1982, "Clinical and experimental studies on retinal neovascularization", Am J Ophthamol 94:715-743.
Pearson and Lipman, 1988, "Improved tools for biological sequence comparison" Proc Natl Acad Sci USA 85:2444-2448.
Polverini et al., 1991, "Assay and purification of naturally occurring inhibitor of angiogenesis", Meth Enzymol 198:440-450.
Quaggio et al., 1993, Protein Science 2: 1053-1056.
Rastinejad et al., 1989, "Regulation of the activity of a new inhibitor of angiogenesis by a cancer suppressor gene", Cell 56:345-355.
Reinach et al., 1998, "Cloning, expression and site-directed mutagenesis of chicken skeletal muscle troponin C", J Biol Chem 263:2371-2376.
Saiki et al., 1989, "Inhibition of the metastasis of murine malignant melanoma by synthetic polymeric peptides containing core sequences of cell-adhesive molecules", Cancer Res. 49: 3815-3822.
Schaub et al., 1969, "The relaxing protein system of striated muscle", Biochem. J. 115:993-1004.
Schreier et al., 1990, "Cloning, structural analysis, and expression of the human slow twitch skeletal muscle/cardiac troponin C gene", J Biol Chem 265:21247-21253.
Sheng et al., 1992, "Isolation, expression and mutation of a rabbit skeletal muscle cDNA clone", J. Biol. Chem., 267: 25407-25413.
Shing et al., 1984, "Heparin affinity: Purification of a tumor-derived capillary endothelial cell growth factor", Science 223:1296-1299.
Shing, 1991, in *Methods of Enzymology*, vol. 198, eds. Barnes, D., Mather, J.P. and Sato, G.H., Academic Press, New York, pp. 91-95.
Smith and Waterman, 1981, "Identification of common molecular subsequences", J Mol Biol 147:195-197.
Tanokura and Ohtsuki, 1984, "Interactions among chymotryptic troponin T subfragments, tropomyosin, troponin I and troponin C" J. Biochem 95:1417-1421.
Taylor and Folkman, 1982, "Protamine is an inhibitor of angiogenesis", Nature 297:307-312.
Teicher et al., 1994, "Potentiation of cytotoxic cancer therapies by TNP-470 alone and with other anti-angiogenic agents", Int J cancer 57:920-925.
Thompson et al., 1994, "Clustal W: improving the sensitivity of progressive multiple sequence alignment through sequence weighting, position-specific gap penalties and weight matrix choice", Nuc Acids Res 22:4673-4680.
Waltman et al., 1978, "Choroidal neovascularization associated with choroidal nevi", Am. J. Ophthalmol. 85: 704-710.
Wu and Wu, 1987, "Receptor-mediated in vitro gene transformation by a soluble DNA carrier system", J Biol Chem 262:4429-4432.
Wu et al., 1994, "Isolation and characterization of human fast skeletal β troponin T cDNA: Comparative sequence analysis is isoforms and insight into the evolution of members of a multigene family", DNA Cell Biol 13:217-233.
Wu and Moses, 1996, Cloning and expression of the cDNA encoding rat tissue inhibitor of metalloproteinase 3 (TIMP-3) Gene 168:243-246.
Xu and Hitchcock-DeGregori, 1988, "Synthesis of a troponin C cDNA and expression of wild-type and mutant proteins in *Escherichia coli*", J Biol Chem 263:735-742.
Yasui et al., 1968, "The role of the sulfhydryl groups of tropomyosin and troponin in the calcium control of actomyosin contractility", J. Biol. Chem. 243:735-742.
Yates and Greaser, 1983, "Troponin subunit stiochiometry and content in rabbit skeletal muscle and myofibrils", J Biol Chem 258:5770-5774.
Zhu et al., 1994, Sequencing of a cDNA encoding the human fast-twitch skeletal muscal isoform of troponin I, Biochim Biophys Acta 1217:338-340.
Moses, M.A. et al., 1999, "Troponin I is present in human cartilage and inhibits angiogenesis," *Proc. Nat'l Acad. Sci.* 96: 2645-2650.
Feldman, L. et al., 2002, "Troponin I inhibits capillary endothelial cell proliferation by interaction with the cell's bFGF receptor," *Microvascular Res.* 63 (1): 41-49.
Vallins, W.J. et al., 1990, "Molecular cloning of human cardiac troponin I using polymerase chain reactions," *FEBS Letters* 270: 57-61.
Wilkinson, J.M. and R.J.A. Grand, 1978, "The Amino-Acid Sequence of Chicken Fast-Skeletal-Muscle Troponin I," *Eur. J. Biochem.* 82: 493-501.

B
```
  1 GCTCTGCAAACAGCTGCACGCCAAGATCGATGCGGCTGAAGAGGAGAAGT
 51 ACGACATGGAGGTGAGGGTGCAGAAGACCAGCAAGGAGCTGGAGGACATG
101 AACCAGAAGCTATTTGATCTGCGGGCCAAGTTCAAGCGGCCCCCACTGCG
151 GAGGGTGCGCATGTCGGCCGATGCCATGCTCAAGGCCCTGCTGGGC
```

FIGURE 7B

A

```
  1 Hu M G D E E K R N R A I T A R R Q H L K S V M L Q I A A T E L E K E E S R R E A E
    Rb - - - - - - - - - - - - - - - - - - - - - - - - - - - - - - G - - - - -

41 Hu K Q N Y L A E H C P P L H I P G S M S E V Q E L C K Q L H A K I D A A E E K Y
    Rb - - - - - - - - - - S L - - - - A - - - - - - - - - - - - - - - - - - - -

93 94
 61 Hu D M E V R V Q K T S K E L E D M N Q K L F D L R G K F K R P P L R R V R M S A D
    Rb - - - I K - - - S - - - - - - - - - - - - - - - - - - - - - - - - - - - -

121 Hu A M L K A L L G S K H K V C K D L R A N L K Q V K K E D T E K E R D L R D V G D
    Rb - - - - - - - - - - - - - - - - - - - - - - - - - - - - - - - - - - - - -

161 Hu W R K N I E E K S G M E G R K K M F E S E S
    Rb - - - - - - - - - - - - - - - - - - - - -
```

METHODS OF INHIBITING ANGIOGENESIS WITH FRAGMENTS AND HOMOLOGS OF TROPONIN SUBUNIT 1

This is a continuation of application Ser. No. 10/176,416, filed Jun. 18, 2002 now U.S. Pat. No. 7,078,385, which is a continuation of U.S. patent application Ser. No. 09/442,099, filed Nov. 17, 1999, now U.S. Pat. No. 6,465,431, which is a continuation-in-part of U.S. patent application Ser. No. 09/268,274, filed Mar. 15, 1999, now abandoned, which is a continuation-in-part of U.S. application Ser. No. 08/961,264, filed Oct. 30, 1997, now U.S. Pat. No. 6,025,331 which is a continuation of U.S. application Ser. No. 08/602,941, filed Feb. 16, 1996, now U.S. Pat. No. 5,837,680.

1. INTRODUCTION

The present invention provides for novel pharmaceutical compositions, and methods of use thereof for the treatment of diseases or disorders involving abnormal angiogenesis.

More particularly, the present invention is based, in part, on the discovery that troponin subunits C, I and T and fragments thereof inhibit stimulated endothelial cell proliferation. Pharmaceutical compositions containing therapeutically effective amounts of troponin C, I, or T, subunits, fragments, or homologs and methods of therapeutic use thereof are provided.

2. BACKGROUND

Angiogenesis, the process of new blood vessel development and formation, plays an important role in numerous physiological events, both normal and pathological. Angiogenesis occurs in response to specific signals and involves a complex process characterized by infiltration of the basal lamina by vascular endothelial cells in response to angiogenic growth signal(s), migration of the endothelial cells toward the source of the signal(s), and subsequent proliferation and formation of the capillary tube. Blood flow through the newly formed capillary is initiated after the endothelial cells come into contact and connect with a preexisting capillary.

The naturally occurring balance between endogenous stimulators and inhibitors of angiogenesis is one in which inhibitory influences predominate. Rastinejad et al., 1989, *Cell* 56:345-355. In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail.

Unregulated angiogenesis becomes pathologic and sustains progression of many neoplastic and non-neoplastic diseases. A number of serious diseases are dominated by abnormal neovascularization including solid tumor growth and metastases, arthritis, some types of eye disorders, and psoriasis. See, e.g., reviews by Moses et al., 1991, *Biotech.* 9:630-634; Folkman et al., 1995, *N. Engl. J. Med.*, 333:1757-1763; Auerbach et al., 1985, *J. Microvasc. Res.* 29:401-411; Folkman, 1985, Advances in Cancer Research, eds. Klein and Weinhouse, Academic Press, New York, pp. 175-203; Patz, 1982, *Am. J. Opthalmol.* 94:715-743; and Folkman et al., 1983, *Science* 221:719-725. In a number of pathological conditions, the process of angiogenesis contributes to the disease state. For example, significant data have accumulated which suggest that the growth of solid tumors is dependent on angiogenesis. Folkman and Klagsbrun, 1987, *Science* 235:442-447.

The maintenance of the avascularity of the cornea, lens, and trabecular meshwork is crucial for vision as well as to ocular physiology. There are several eye diseases, many of which lead to blindness, in which ocular neovascularization occurs in response to the diseased state. These ocular disorders include diabetic retinopathy, neovascular glaucoma, inflammatory diseases and ocular tumors (e.g., retinoblastoma). There are also a number of other eye diseases which are also associated with neovascularization, including retrolental fibroplasia, uveitis, retinopathy of prematurity, macular degeneration, and approximately twenty eye diseases which are associated with choroidal neovascularization and approximately forty eye diseases associated with iris neovascularization. See, e.g., reviews by Waltman et al., 1978, *Am. J. Ophthal.* 85:704-710 and Gartner et al., 1978, *Surv. Ophthal.* 22:291-312. Currently, the treatment of these diseases, especially once neovascularization has occurred, is inadequate and blindness often results. Studies have suggested that vasoinhibitory factors which are present in normal ocular tissue (cornea and vitreous) are lost in the diseased state.

An inhibitor of angiogenesis could have an important therapeutic role in limiting the contributions of this process to pathological progression of the underlying disease states as well as providing a valuable means of studying their etiology. For example, agents that inhibit tumor neovascularization could play an important role in inhibiting metastatic tumor growth.

The components of angiogenesis relating to vascular endothelial cell proliferation, migration and invasion, have been found to be regulated in part by polypeptide growth factors. Experiments in culture, indicate that endothelial cells exposed to a medium containing suitable growth factors can be induced to evoke some or all of the angiogenic responses. Several polypeptides with in vitro endothelial growth promoting activity have been identified. Examples include acidic and basic fibroblast growth factors, transforming growth factors α and β platelet-derived endothelial cell growth factor, granulocyte colony-stimulating factor, interleukin-8, hepatocyte growth factor, proliferin, vascular endothelial growth factor and placental growth factor. See, e.g., review by Folkman et al., 1995, *N. Engl. J. Med.*, 333:1757-1763.

Although extracts from several different tissue sources have been shown to contain anti-angiogenic activity, several molecules such as platelet factor-4, thrombospondin, protamine, and transforming growth factor B, have been found to negatively regulate different aspects of angiogenesis, such as cell proliferation or cell migration. No single tissue-derived macromolecule capable of inhibiting angiogenesis has been identified in the prior art. See, e.g., reviews by Folkman, J., 1995, *N. Engl. J. Med.* 333:1757-1763 and D'Amore, 1985, *Prog. Clin. Biol. Res.* 221:269-283. There is therefore a great need for the further identification and characterization of chemical agents which can prevent the continued deregulated spread of vascularization and which would potentially have broad applicability as a therapy for those diseases in which neovascularization plays a prominent role.

Capillary endothelial cells ("EC") proliferate in response to an angiogenic stimulus during neovascularization. Ausprunk and Folkman, 1977, *J. Microvasc. Res.* 14:153-65. An in vitro assay assessing endothelial cell proliferation in response to known angiogenesis simulating factors, such as acidic or basic fibroblast growth factor (aFGF and bFGF, respectively), has been developed to mimic the process of neovascularization in vitro. This type of assay is the assay of choice to demonstrate the stimulation of capillary EC proliferation by various angiogenic factors. Shing et al., 1984, *Science* 223:1296-1298.

The process of capillary EC migration through the extracellular matrix towards an angiogenic stimulus is also a critical event required for angiogenesis. See, e.g., review by Ausprunk et al., 1977, *J. Microvasc. Res.* 14:53-65. This process provides an additional assay by which to mimic the process of neovascularization in vitro. A modification of the Boyden chamber technique has been developed to monitor EC migration. Boyden et al., 1962, *J. Exptl. Med.* 115:453-456, Example 4. To date, only a few tissue-derived EC cell migration inhibitors are known. See, e.g., review by Langer et al., 1976, *Science* 193:70-72.

In the early 1970's, a number of in vivo angiogenesis model bioassays were widely used. These model systems included rabbit corneal pocket, chick chorioallantoic membrane ("CAM"), rat dorsal air sac and rabbit air chamber bioassays. For review, see, Blood et al., 1990, *Biochem. et Biophys. Acta* 1032:89-118. The development of controlled release polymers capable of releasing large molecules such as angiogenesis stimulators and inhibitors was critical to the use of these assays. Langer et al., 1976, *Nature* 263:797-800.

In the CAM bioassay, fertilized chick embryos are cultured in Petri dishes. On day 6 of development, a disc of a release polymer, such as methyl cellulose, impregnated with the test sample or an appropriate control substance is placed onto the vascular membrane at its advancing edge. On day 8 of development, the area around the implant is observed and evaluated. Avascular zones surrounding the test implant indicate the presence of an inhibitor of embryonic neovascularization. Moses et al., 1990, *Science*, 248:1408-1410 and Taylor et al., 1982, *Nature*, 297:307-312. The reported doses for previously described angiogenesis inhibitors tested alone in the CAM assay are 50 μg of protamine (Taylor et al. (1982)), 200 μg of bovine vitreous extract (Lutty et al., 1983, *Invest. Opthalmol. Vis. Sci.* 24:53-56), and 10 μg of platelet factor IV (Taylor et al. (1982)). The lowest reported doses of angiogenesis inhibitors effective as combinations include heparin (50 μg) and hydrocortisone (60 μg), and B-cyclodextrin tetradecasulfate (14 μg) and hydrocortisone (60 μg), reported by Folkman et al., 1989, *Science* 243:1490.

According to the rabbit corneal pocket assay, polymer pellets of ethylene vinyl acetate copolymer ("EVAC") are impregnated with test substance and surgically implanted in a pocket in the rabbit cornea approximately 1 mm from the limbus. Langer et al., 1976, *Science* 193:707-72. To test for an angiogenesis inhibitor, either a piece of carcinoma or some other angiogenic stimulant is implanted distal to the polymer 2 mm from the limbus. In the opposite eye of each rabbit, control polymer pellets that are empty are implanted next to an angiogenic stimulant in the same way. In these control corneas, capillary blood vessels start growing towards the tumor implant in 5-6 days, eventually sweeping over the blank polymer. In test corneas, the directional growth of new capillaries from the limbal blood vessel towards the tumor occurs at a reduced rate and is often inhibited such that an avascular region around the polymer is observed. This assay is quantitated by measurement of the maximum vessel lengths with a stereospecific microscope.

Troponin, a complex of three polypeptides is an accessory protein that is closely associated with actin filaments in vertebrate muscle. The troponin complex, acts in conjunction with the muscle form of tropomyosin to mediate the $Ca^{2+}$ dependency of myosin ATPase activity and thereby regulate muscle contraction. The troponin polypeptides T, I, and C, are named for their tropomyosin binding, inhibitory, and calcium binding activities, respectively. Troponin T binds to tropomyosin and is believed to be responsible for positioning the troponin complex on the muscle thin filament. Troponin I binds to actin, and the complex formed by troponins I and T, and tropomyosin, inhibits the interaction of actin and myosin. Troponin C is capable of binding up to four calcium molecules. Studies suggest that when the level of calcium in the muscle is raised, troponin C causes troponin I to loose its hold on the actin molecule, causing the tropomyosin molecule shift, thereby exposing the myosin binding sites on actin and stimulating myosin ATPase activity.

The citation of a reference herein shall not be construed as an admission that such reference is prior art to the present invention.

3. SUMMARY OF THE INVENTION

The present invention relates to pharmaceutical compositions containing troponin subunits C, I, or T, or fragments thereof, in therapeutically effective amounts that are capable of inhibiting angiogenesis, for example, by inhibiting endothelial cell proliferation. The invention also relates to pharmaceutical compositions containing homologs of troponin subunits C, I, or T and homologs of their fragments, in therapeutically effective amounts that are capable of inhibiting angiogenesis, for example, by inhibiting endothelial cell proliferation. The invention further relates to treatment of neovascular disorders by administration of a therapeutic compound of the invention. Such therapeutic compounds (termed herein "Therapeutics"), include: troponin subunits C, I, and T, and fragments and homologs thereof, in particular, fragments of troponin subunit I comprising the inhibitory (I') and carboxy terminal (C') regions. In one embodiment, a Therapeutic of the invention is administered to treat a cancerous condition, for example, to inhibit the growth or reduce the volume of a solid tumor, or to prevent progression from the pre-neoplastic or pre-malignant state into a neoplastic or a malignant state or to inhibit metastasis. In other specific embodiments, a Therapeutic of the invention is administered to treat ocular disorders associated with neovascularization. As used herein, the term "troponin subunit", when not preceding the terms C, I or T, means generically any of troponin subunits C, I, or T. The amino-terminal, inhibitory and carboxy-terminal regions of troponin I are designated N', I', and C', respectively.

4. BRIEF DESCRIPTION OF THE FIGURES

FIG. 1. Inhibition of bovine capillary Endothelial Cell (BCE) proliferation by troponin C. Percent inhibition of bFGF-stimulated BCE proliferation is shown as a function of troponin C concentration (μg/well). Percent inhibition was determined by comparing results obtained for cells treated with stimulus alone with those obtained for samples exposed to both stimulus and inhibitor. Well volume was 200 μl.

FIG. 2. Inhibition of capillary BCE proliferation by troponin I. Percent inhibition of bFGF-stimulated BCE proliferation is shown as a function of troponin I concentration (μg/well). Percent inhibition was determined as described in FIG. 1. Well volume was 200 μl.

FIG. 3. Inhibition of capillary BCE proliferation by troponin T. Percent inhibition of bFGF-stimulated BCE proliferation is shown as a function of troponin T concentration (μg/well). Percent inhibition was determined as described in FIG. 1. Well volume was 200 μl.

FIG. 4. Inhibition of BCE proliferation by troponins C and I. Percent inhibition of bFGF-stimulated BCE proliferation is shown as a function of troponin I and C concentration (µg/well). Percent inhibition was determined as described in FIG. 1. Well volume was 200 µl.

FIG. 5. Inhibition of capillary BCE proliferation by troponin C, I and T. Percent inhibition of bFGF-stimulated BCE proliferation is shown as a function of troponin C, I, and T concentration (μg/well). Percent inhibition was determined as described in FIG. 1. Well volume was 200 μl.

FIG. 6. Schematic representation of amino acid sequences of tryptic peptides (LQIAATELEK, SEQ ID NO:18; IDVAEEEKYDMEVK, SEQ ID NO:19; AND LFDLR, SEQ ID NO:20) purified from cartilage as described in Methods. Sequence similarity to human TnI is indicated by alignment with the amino acid sequence of the human isoform.

FIG. 7. (A) RT-PCR products amplified from total RNA purified from two separate human intercostal cartilage specimens. Gene-specific primers were designed based on the cDNA sequence of human fast-twitch skeletal muscle TnI. (B) Nucleotide sequence of these PCR products showing identity to the cDNA sequence of human fast-twitch skeletal muscle TnI (nt 189-nt 384) (SEQ ID NO:16). (C) RT-PCR amplification, from total RNA (20 ng each lane) purified from rat skeletal muscle (lane 1), xyphoid (lane 2), chondrosarcoma (lane 3) and liver (lane 4). Gene-specific primers were designed based on the cDNA sequence of rat fast-twitch skeletal muscle TnI as described in Methods.

FIG. 8. SDS-PAGE of recombinant human TnI before (lane A) and after (lane B) purification. In both cases, approximately 1 μg of total protein was electrophoresed, followed by silver staining as described in Methods. Recombinant TnI migrates at a molecular weight of approximately 21,000 Da.

FIG. 9. Inhibition of capillary EC proliferation by rTnI. Percent inhibition was determined by comparing wells exposed to the angiogenic stimulus bFGF (A) and VEGF (B) with those exposed to stimulus and inhibitor. Each point represents the mean of duplicate control and inhibitor wells. This is a representative experiment of four different EC proliferation assays, each testing different TnI preparations.

FIG. 10. Inhibition of embryonic angiogenesis in vivo by rTnI. After a 48 h exposure to rTnI as described in Methods, avascular zones, free of capillaries and small vessels were observed using a binocular dissecting microscope at ×7-10 magnification. This zone was produced by approximately 380 pmoles of TnI (A). A normal chorioallantoic membrane (CAM) implanted with a methylcellulose disk containing buffer alone is shown in (B).

FIG. 11. Inhibition of FGF induced angiogenesis by systemic administration of TnI. TnI (50 mg/kg) was administered systemically every 12 hours to mice whose corneas had been implanted with pellets containing bFGF (40 ng/ml) on Day 1. After-six days of treatment, significant inhibition of FGF-induced neovascularization was observed in TnI-treated corneas (B) as compared to control corneas (A).

FIG. 12. (A) Derived amino acid sequence of recombinant human TnI (Hu)(SEQ ID NO:17) and its sequence comparison with recombinant rabbit TnI (Rb) (SEQ ID NO:10). Identical residues are shown by dashes. (B) Schematic representation of various recombinant TnI deletion fragments based on rabbit TnI and wild-type rabbit TnI, (SEQ ID NO:10). The troponin I inhibitory region is designated I', and the sequences located on amino- and carboxy-terminal sides of this region are designated N' and C', respectively. $TnI_{1-120}$, $TnI_{1-94}$, $TnI_{96-181}$, $TnI_{122-181}$ contain the N' and I', N', I' and C', and C' regions, respectively. The number of amino acids at the beginning and end of each fragment is indicated. $TnI_{98-114}$ containing amino acid residues 98-114 is a synthetic peptide representing the I region.

5. DETAILED DESCRIPTION OF THE INVENTION

The present invention relates to therapeutic methods and compositions based on troponin subunits. The invention provides for treatment of neovascular disorders by, for example, inhibiting angiogenesis, comprising administration of a therapeutic compound of the invention. Such therapeutic compounds (termed herein "Therapeutics") include: troponin C, I, and T subunits, fragments and homologs thereof (collectively "peptides of the invention"). The peptides of the invention are characterized by the property of inhibiting bovine endothelial cell (EC) proliferation in culture preferably with an $IC_{50}$ of about 10 μM or less, more preferably with an $IC_{50}$ of about 5 μM or less, most preferably with an $IC_{50}$ of about 1 μM or less. In a preferred embodiment, a Therapeutic of the invention is administered to treat a cancerous condition, for example, to inhibit the growth or reduce the volume of a solid tumor, or to prevent progression from a pre-neoplastic or non-malignant state into a neoplastic or a malignant state or to inhibit metastases. In another specific embodiment, a Therapeutic of the invention is administered to treat an ocular disorder associated with neovascularization.

In a preferred aspect, a Therapeutic of the invention is a peptide consisting of at least a fragment of troponin C, troponin I, troponin T, or combinations thereof which is effective to inhibit angiogenesis. More preferably, the Therapeutic is a peptide consisting of the inhibitory (I') and carboxy terminal (C') region (C'+I') (SEQ ID NO:14) of troponin subunit I or a fragment thereof.

In specific embodiments, the peptides of the invention are troponin C, troponin I and troponin T subunits, or fragments thereof of the fast twitch, slow twitch and cardiac isoforms from mammalian species, e.g., human, rabbit, rat, mouse, bovine, ovine and porcine.

In other embodiments, the peptides of the invention are troponin C, troponin I and troponin T subunits, or fragments thereof from nonmuscle tissues, e.g., cartilage, preferably from mammalian species, e.g., human, rabbit, rat, mouse, bovine, ovine and porcine.

Examples of the troponin subunits that can be utilized in accordance with the invention, include but are not limited to the subunits of troponin from human fast twitch skeletal muscle, the sequences of which are given below:

| Fast Twitch Skeletal Muscle Troponin C (SEQ ID NO:1) | |
|---|---|
| 1 | M T D Q Q A E A R S Y L S E E M I A E F |
| 21 | K A A F D M F D A D G G G D I S V K E L |
| 41 | G T V M R M L G Q T P T K E E L D A I I |
| 61 | E E V D E D G S G T I D F E E F L V M M |
| 81 | V R Q M K E D A K G K S E E E L A E C F |
| 101 | R I F D R N A D G Y I D P E E L A E I F |
| 121 | R A S G E H V T D E E I E S L M K D G D |
| 141 | K N N D G R I D F D E F L K M M E G V Q |

| Fast Twitch Skeletal Muscle Troponin I (SEQ ID NO:2) |
| --- |
| 1   M G D E E K R N R A I T A R R Q H L K S |
| 21  V M L Q I A A T E L E K E E S R R E A E |
| 41  K Q N Y L A E H C P P L H I P G S M S E |
| 61  V Q E L C K Q L H A K I D A A E E E K Y |
| 81  D M E V R V Q K T S K E L E D M N Q K L |
| 101 F D L R G K F K R P P L R R V R M S A D |
| 121 A M L K A L L G S K H K V C M D L R A N |
| 141 L K Q V K K E D T E K E R D L R D V G D |
| 161 W R K N I E E K S G M E G R K K M F E S |
| 181 E S |

| Fast Skeletal Beta Troponin T (SEQ ID NO:3) |
| --- |
| 1   M S D E E V E Q V E E Q Y E E E E E A Q |
| 21  E E E E V Q E D T A E E D A E E E K P R |
| 41  P K L T A P K I P E G E K V D F D D I Q |
| 61  K K R Q N K D L M E L Q A L I D S H F E |
| 81  A R K K E E E E L V A L K E R I E K R R |
| 101 A E R A E Q Q R I R A E K E R E R Q N R |
| 121 L A E E K A R R E E E D A K R R A E D D |
| 141 L K K K K A L S S M G A N Y S S Y L A K |
| 161 A D Q K R G K K Q T A R E M K K K I L A |
| 181 E R R K P L N I D H L G E D K L R D K A |
| 201 K E L W E T L H Q L E I D K F E F G E K |
| 221 L K R Q K Y D I T T L R S R I D Q A Q K |
| 241 H S K K A G T P A K G K V G G R W K |

In another embodiment, the invention encompasses peptides which are homologous to troponin C (SEQ ID NO:1) or fragments thereof, troponin I (SEQ ID NOS:2, 10, or 15) or fragments thereof, or troponin T (SEQ ID NO:3) or fragments thereof.

In a particular embodiment, the peptides of the invention are fragments of troponin I (SEQ ID NOS:11-15) or homologous to fragments of troponin I (SEQ ID NOS:11-15).

In a specific embodiment, a Therapeutic of the invention is combined with a therapeutically effective amount of another molecule which negatively regulates angiogenesis which may be, but is not limited to, platelet factor 4, thrombospondin-1, tissue inhibitors of metalloproteases (TIMP1 and TIMP2) prolactin (16-Kd fragment), angiostatin (38-Kd fragment of plasminogen), bFGF soluble receptor, transforming growth factor β, interferon alfa, and placental proliferin-related protein.

Paradoxically, neovascularization gradually reduces a tumor's accessibility to chemotherapeutic drugs due to increased interstitial pressure within the tumor, which causes vascular compression and central necrosis. In vivo results have demonstrated that rodents receiving angiogenic therapy show increased delivery of chemotherapy to a tumor. Teicher et al., 1994, *Int. J. Cancer* 57:920-925. Thus, in one embodiment, the invention provides for a pharmaceutical composition of the present invention in combination with a chemotherapeutic agent.

In another preferred aspect, a Therapeutic of the invention is combined with chemotherapeutic agents or radioactive isotope exposure.

The invention is illustrated by way of examples infra which disclose, inter alia, the inhibition of capillary endothelial cell proliferation by troponin subunits C, I, and T and the means for determining inhibition of capillary endothelial cell migration and inhibition of neovascularization in vivo by troponin subunits.

For clarity of disclosure, and not by way of limitation, the detailed description of the invention is divided into the subsections set forth below.

5.1. Troponin Subunits, Fragments and Homologs

The invention provides for pharmaceutical compositions comprising troponin subunits, fragments, and homologs thereof. In particular aspects, the subunits, fragments, or homologs are of fly, frog, mouse, rat, rabbit, pig, cow, dog, monkey, or human troponin subunits.

In another embodiment, the invention encompasses peptides which are homologous to troponin C (SEQ ID NO:1) or fragments thereof. In one embodiment, the amino acid sequence of the peptide has at least 80% identity compared to the troponin C from which it is derived. In another embodiment, this identity is greater than 85%. In a more preferred embodiment, this identity is greater than 90%. In a most preferred embodiment, the amino-acid sequence of the peptide has at least 95% identity with the troponin C or fragment thereof. Fragments are generally at least 10 amino acids, and in alternate embodiments at least 20, 30, 40, 50, 75, and 100 amino acids in length.

In another embodiment, the invention encompasses a troponin submit subunit or fragment thereof encoded by a nucleic acid hybridizable to the complement of a nucleic acid encoding a troponin subunit, preferably troponin C, under low stringency, moderate stringency or high stringency conditions.

In another embodiment, the invention encompasses peptides which are homologous to troponin I(SEQ ID NOS:2, 10 or 15) or fragments thereof. In one embodiment, the amino acid sequence of the peptide has at least 80% identity with the troponin I or fragment thereof. In another embodiment, this identity is greater than 85%. In a more preferred embodiment, this identity is greater than 90%. In a most preferred embodiment, the amino acid sequence of the peptide has at least 95% identity with the troponin I or fragment thereof. Fragments are generally at least 4 amino acids, and in alternate embodiments at least 8, 10, 20, 30, 40, 50, 75, and 100 amino acids in length.

In another embodiment, the invention encompasses a troponin submit subunit or fragment thereof encoded by a nucleic acid hybridizable to the complement of a nucleic acid encoding a troponin subunit, preferably troponin I, under low stringency, moderate stringency or high stringency conditions.

In another embodiment, the invention encompasses peptides which are homologous to troponin T (SEQ ID NO:3) or fragments thereof. In one embodiment, the amino acid sequence of the peptide has at least 80% identity with the troponin T or fragment thereof. In another embodiment, this identity is greater than 85%. In a more preferred embodiment, this identity is greater than 90%. In a most preferred embodiment, the amino acid sequence of the peptide has at least 95% identity with the troponin T or fragment thereof. Fragments are generally at least 10 amino acids, and in alternate embodiments at least 20, 30, 40, 50, 75, 100, 150, and 200 amino acids in length.

In another embodiment, the invention encompasses a troponin submit subunit or fragment thereof encoded by a nucleic acid hybridizable to the complement of a nucleic acid encoding a troponin subunit, preferably troponin T, under low stringency, moderate stringency or high stringency conditions.

In a preferred embodiment, the invention encompasses peptides which are homologous to the Inhibitory (I') and carboxy terminus (C') region (C'+I') (SEQ ID NO: 14). In other embodiments, the invention encompasses peptides that are homologous to the C'+I' region of human troponin I (huTnI) (SEQ ID NO:17) corresponding to amino acid residues of SEQ ID NO:17, including but not limited to residues: 94-123 (huTnI$_{94-123}$), 104-133 (huTnI$_{104-133}$), 114-143 (huTnI$_{114-143}$), 129-153 (huTnI$_{129-153}$), 134-173 (huTnI$_{134-173}$), 144-182 (huTnI$_{144-182}$), 93-112 (huTnI$_{93-112}$), 98-117 (huTnI$_{98-117}$), 103-122 (huTnI$_{103-122}$), 108-127 (huTnI$_{108-127}$), 113-132 (huTnI$_{113-132}$), and carboxy terminus region (C'), 118-137 (huTnI$_{118-137}$).

Additional embodiments include 94-113 (huTnI.sub.94-113), 98-117 (huTnI$_{98-117}$), 102-121 (huTnI$_{102-121}$), 106-125 (huTnI$_{106-125}$) 110-129 (huTnI$_{110-129}$), and 114-133 (huTnI$_{114-133}$). Still other embodiments include carboxy terminus region (C') of human troponin I (huTnI), 116-123 (huTnI$_{116-123}$), 118-125 (huTnI$_{118-125}$) 120-127 (huTnI$_{120-127}$) 122-129 (huTnI$_{122-129}$), 124-131 (huTnI$_{124-131}$), 126-133 (huTnI$_{126-133}$), 128-135 (huTnI$_{128-135}$), 130-137 (huTnI$_{130-137}$), 132-139 (huTnI$_{132-139}$), 134-141 (huTnI$_{134-141}$), and 136-143 (huTnI$_{136-143}$). Fragments are generally at least 4 amino acids, and in alternate embodiments at least 8, 10, 20, 30, 40, 50, and 75 amino acids in length.

"Homologous," as defined herein, refers to identity over an amino acid sequence of identical size or when compared to an aligned sequence in which the alignment is done by a computer homology program known in the art or whose encoding nucleic acid is capable of hybridizing to a coding gene sequence, under high stringency, moderate stringency, or low stringency conditions.

Specifically, by way of example, computer programs for determining homology may include but are not limited to TBLASTN, BLASTP, FASTA, TEASTA, and CLUSTALW (Pearson and Lipman, 1988, Proc. Natl. Acad. Sci. USA 85(8):2444-8; Altschul et al., 1990, J. Mol. Biol. 215(3):403-10; Thompson, et al., 1994, Nucleic Acids Res. 22(22):4673-80; Higgins, et al., 1996, Methods Enzymol 266:383-402; Altschul, et al., 1990, J. Mol. Biol. 215(3):403-10). Default parameters for each of these computer programs are well known and should be utilized.

Specifically, Basic Local Alignment Search Tool (BLAST) (www.ncbi.nlm.nih.gov; It is to be understood that for determination of homology, the default parameters are set and utilized with the most recent BLAST program version available at this site.) (Altschul et al., 1990, J. of Molec. Biol., 215:403-410, "The BLAST Algorithm; Altschul et al., 1997, Nuc. Acids Res. 25:3389-3402) is a heuristic search algorithm tailored to searching for sequence similarity which ascribes significance using the statistical methods of Karlin and Altschul 1990, Proc. Natl Acad. Sci. USA, 87:2264-68; 1993, Proc. Nat'l Acad. Sci. USA 90:5873-77. Five specific BLAST programs perform the following tasks: 1) The BLASTP program compares an amino acid query sequence against a protein sequence database; 2) The BLASTN program compares a nucleotide query sequence against a nucleotide sequence database; 3) The BLASTX program compares the six-frame conceptual translation products of a nucleotide query sequence (both strands) against a protein sequence database; 4) The TBLASTN program compares a protein query sequence against a nucleotide sequence database translated in all six reading frames (both strands); 5) The TBLASTX program compares the six-frame translations of a nucleotide query sequence against the six-frame translations of a nucleotide sequence database.

Smith-Waterman (database: European Bioinformatics Institute wwwz.ebi.ac.uk/bic_sw/) (Smith-Waterman, 1981, J. of Molec. Biol., 147:195-197) is a mathematically rigorous algorithm for sequence alignments.

FASTA (see Pearson et al., 1988, Proc. Nat'l Acad. Sci. USA, 85:2444-2448) is a heuristic approximation to the Smith-Waterman algorithm. For a general discussion of the procedure and benefits of the BLAST, Smith-Waterman and FASTA algorithms see Nicholas et al., 1998, "A Tutorial on Searching Sequence Databases and Sequence Scoring Methods" (www.psc.edu) and references cited therein.

It is envisioned that troponin subunits and fragments can be made by altering troponin sequences by substitutions, additions or deletions that provide for functionally equivalent molecules capable of displaying one or more functional activities associated with a full-length wild-type troponin subunit. Such functional activities include but are not limited to inhibition of angiogenesis; inhibition of metastases; inhibition of tumor growth. These include, but are not limited to, troponin subunits, fragments, or homologs containing, as a primary amino acid sequence, all or part of the amino acid sequence of a troponin subunit including altered sequences in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

One embodiment of the invention provides for molecules consisting of or comprising a fragment of at least 4 (contiguous) amino acids of a troponin subunit which is capable of inhibiting endothelial cell proliferation as discussed above. In other embodiments, this molecule consists of at least 8, 10, 20 or 50 amino acids of the troponin subunit. In specific embodiments, such molecules consist of or comprise fragments of a troponin subunit that are at least 8, 10, 20, 30, 40, 50, 75, 100 and 150 amino acids in length, including but not limited to, C'+I' (SEQ ID NO:14), huTnI$_{94-123}$, huTnI$_{104-133}$, huTnI$_{114-143}$, huTnI129-153, huTnI$_{134-173}$, huTnI$_{144-182}$, huTnI$_{93-112}$, huTnI$_{98-112}$, huTnI$_{103-122}$, huTnI$_{108-127}$, huTnI$_{113-132}$, and carboxy terminus region (C') huTnI$_{118-137}$.

Additional embodiments include 94-113 (huTnI$_{94-113}$) 98-117 (huTnI$_{98-117}$), 102-121 (huTnI$_{102-121}$), 106-125 (huTnI$_{106-125}$), 110-129 (huTnI$_{110-129}$), and 114-133 (huTnI$_{114-133}$). Still other embodiments include carboxy terminus region (C'), 116-123 (huTnI$_{116-123}$), 118-125 (huTnI$_{118-125}$), 120-127 (huTnI$_{120-127}$), 122-129 (huTnI$_{122-129}$), 124-131 (huTnI$_{124-131}$), 126-133 (huTnI$_{126-133}$), 128-135 (huTnI$_{128-135}$), 130-137 (huTnI$_{130-137}$), 132-139 (huTnI$_{132-139}$), 134-141 (huTnI$_{134-141}$), and 136-143 (huTnI$_{136-143}$).

In a preferred embodiment, the protein is a mammalian troponin subunit. In more preferred embodiments, it is a mammalian troponin C, I, or T subunit.

The troponin subunits, fragments and homologs of the invention can be derived from tissue (see, for example, Section 6, Examples 1 and 7; Ebashi et al., 1968, *J. Biochem.* 64:465; Yasui et al., 1968, J. Riol. Chem. 243:735; Hartshorne et al., 1968, *Biochem. Biophys. Res. Commun.* 31:647; Shaub et al., 1969, *Biochem. J.* 115:993; Greaser et al., 1971, *J. Biol. Chem.* 246:4226-4733; Brekke et al., 1976, *J. Biol. Chem.* 251:866-871; and Yates et al., 1983, *J. Biol. Chem.* 258:5770-5774) or produced by various methods known in the art, for example, recombinant techniques (see; for example, Section 6, Examples 1 and 7).

Manipulations of troponin subunits can occur at the gene or protein level. For example, a cloned troponin gene sequence coding for troponin subunits C, I, or T, can be modified by any of numerous strategies known in the art. Sambrook et al., 1989, Molecular Cloning, A Laboratory Manual, 2d ed., Cold Spring Harbor Laboratory, Cold Spring Harbor, N.Y. The sequence can be cleaved at appropriate sites with restriction endonuclease(s), followed by further enzymatic modification if desired, isolated, and ligated in vitro. In the production of the gene encoding a fragment or homolog of a troponin subunit, care should be taken to ensure that the modified gene remains within the same translational reading frame as the troponin subunit gene, uninterrupted by translational stop signals, in the gene region where the desired troponin activity is encoded.

In a specific embodiment, a nucleic acid which is hybridizable to the complement of a troponin nucleic acid (e.g., having a sequence as set forth in SEQ ID NOS:13-17), or to a nucleic acid encoding a troponin fragment or derivative under conditions of low stringency is provided. By way of example and not limitation, procedures using such conditions of low stringency are as follows (see also Shilo and Weinberg, 1981, Proc. Natl. Acad. Sci. U.S.A. 78, 6789-6792). Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10$^6$ cpm $^{32}$P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65-68° C. and re-exposed to film. Other conditions of low stringency which may be used are well known in the art (e.g., as employed for cross-species hybridizations).

In another specific embodiment, a nucleic acid which is hybridizable to a troponin nucleic acid under conditions of high stringency is provided. By way of example and not limitation, procedures using such conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5-20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

In another specific embodiment, a nucleic acid which is hybridizable to a troponin nucleic acid under conditions of moderate stringency is provided. Selection of appropriate conditions for such stringencies is well known in the art (see e.g., Sambrook et al., 1989, Molecular Cloning, A Laboratory Manual, 2d Ed., Cold Spring Harbor Laboratory Press, Cold Spring Harbor, N.Y.; see also, Ausubel et al., eds., in the Current Protocols in Molecular Biology series of laboratory technique manuals, © 1987-1997 Current Protocols, © 1994-1997 John Wiley and Sons, Inc.).

Additionally, the troponin subunit encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including, but not limited to, in vitro site-directed mutagenesis (Hutchinson et al., 1978, *J. Biol. Chem.* 253:6551), use of TAB® linkers (Pharmacia), etc.

Manipulations of troponin subunit C, I, or T sequence may also be made at the protein level. Included within the scope of the invention are troponin subunit fragments or other fragments or homologs which are differentially modified during or after translation, e.g., by acetylation, phosphorylation, carboxylation, amidation, derivatization by known protecting/blocking groups, proteolytic cleavage, linkage to an antibody molecule or other cellular ligand, etc. Any of numerous chemical modifications may be carried out by known techniques, including, but not limited to, specific chemical cleavage by cyanogen bromide, trypsin, chymotrypsin, papain, V8 protease, NaBH$_4$, acetylation, formylation, oxidation, reduction, etc.

In addition, fragments and homologs of troponin subunits can be chemically synthesized. For example, a peptide corresponding to a portion of a troponin subunit which comprises the desired domain, or which mediates the desired activity in vitro, can be synthesized by use of a peptide synthesizer. Furthermore, if desired, nonclassical amino acids or chemical amino acid homologs can be introduced as a substitution or addition into the troponin subunit sequence. Non-classical amino acids include, but are not limited to, the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, C α-methyl amino acids, and Nα methyl amino acids.

In a specific embodiment, the invention encompasses a chimeric, or fusion, protein comprising a troponin subunit or fragment thereof (consisting of at least a domain or motif of the troponin subunit that is responsible for inhibiting endothelial cell proliferation) joined at its amino or carboxy-terminus via a peptide bond to an amino acid sequence of a different protein. Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

In another embodiment, the invention encompasses combination of the troponin subunits, fragments, or homologs of the present invention to inhibit angiogenesis. Another embodiment provides for the-combination of troponin subunits, fragments, or homologs with other angiogenesis inhibiting factors. Such angiogenesis inhibiting factors include, but are not limited to: angiostatic steroids, thrombospondin, platelet factor IV, transforming growth factor β, interferons, tumor necrosis factor α, bovine vitreous extract, protamine, tissue inhibitors of metalloproteinases (TIMP-1 and TIMP-2), prolactin (16-kd fragment), angiostatin (38-kd fragment of plasminogen), bFGF soluble receptor, and placental proliferin-related protein. See, e.g., reviews by Folkman et al., 1995, *N. Engl. J. Med.* 333:1757-1763 and Klagsbrun et al., 1991, *Annu. Rev. Physiol.* 53:217-239.

5.2. Assays of Troponin Proteins Fragments and Homologs

The functional activity and/or therapeutically effective dose of troponin subunits, fragments and homologs, can be assayed in vitro by various methods. These methods are based on the physiological processes involved in angiogenesis and while they are within the scope of the invention, they are not intended to limit the methods by which troponin subunits, fragments and homologs inhibiting angiogenesis are defined and/or a therapeutically effective dosage of the pharmaceutical composition is determined.

For example, where one is assaying for the ability of troponin subunits, fragments, and homologs, to inhibit or interfere with the proliferation of capillary endothelial cells (EC) in vitro, various bioassays known in the art can be used, including, but not limited to, radioactive incorporation into nucleic acids, calorimetric assays and cell counting.

Inhibition of endothelial cell proliferation may be measured by calorimetric determination of cellular acid phosphatase activity or electronic cell counting. These methods provide a quick and sensitive screen for determining the number of endothelial cells in culture after treatment with the troponin subunit, fragment, or homolog of the invention, and an angiogenesis stimulating factor such as aFGF. The calorimetric determination of cellular acid phosphatase activity is described by Connolly et al., 1986, *J. Anal. Biochem.* 152: 136-140. According to this method, described in Example 9, capillary endothelial cells are treated with angiogenesis stimulating factors, such as aFGF, and a range of potential inhibitor concentrations. These samples are incubated to allow for growth, and then harvested, washed, lysed in a buffer containing a phosphatase substrate, and then incubated a second time. A basic solution is added to stop the reaction and color development is determined at 405 λ. According to Connolly et al., a linear relationship is obtained between acid phosphatase activity and endothelial cell number up to 10,000 cells/sample. Standard curves for acid phosphatase activity are also generated from known cell numbers in order to confirm that the enzyme levels reflect the actual EC numbers.

Percent inhibition is determined by comparing the cell number of samples exposed to stimulus with those exposed to both stimulus and inhibitor.

Colorimetric assays to determine the effect of troponin subunits C, I, and T on endothelial cell proliferation demonstrate that all three troponin subunits interfere with bFGF-stimulated endothelial cell proliferation but have no detectable inhibitory effect on the growth of Balb/c 3T3 cells, a non-endothelial cell line. For an illustrative example, see Section 6, Examples 3 and 8, infra.

The incorporation of radioactive thymidine by capillary endothelial cells represents another means by which to assay for the inhibition of endothelial cell proliferation by a potential angiogenesis inhibitor. According to this method, a predetermined number of capillary endothelial cells are grown in the presence of $^3$H-Thymidine stock, an angiogenesis stimulator such as for example, bFGF, and a range of concentrations of the angiogenesis inhibitor to be tested. Following incubation, the cells are harvested and the extent of thymidine incorporation is determined. See, e.g., Section 6, Example 3.

The ability of varying concentrations of troponin subunits, fragments or homologs to interfere with the process of capillary endothelial cell migration in response to an angiogenic stimulus can be assayed using the modified Boyden chamber technique. See, e.g., Section 6, Example 4, infra.

Another means by which to assay the functional activity of troponin subunits, fragments and homologs, involves examining the ability of the compounds to inhibit the directed migration of capillary endothelial cells which ultimately results in capillary tube formation. This ability may be assessed for example, using an assay in which capillary endothelial cells plated on collagen gels are challenged with the inhibitor, and determining whether capillary-like tube structures are formed by the cultured endothelial cells.

Assays for the ability to inhibit angiogenesis in vivo include the chorioallantoic membrane assay and corneal pocket assays (see, e.g., Section 6, infra, Example 10, and Example 11, respectively). See also, Polverini et al., 1991, *Methods Enzymol.* 198:440-450. According to the corneal pocket assay, a tumor of choice is implanted into the cornea of the test animal in the form of a corneal pocket. The potential angiogenesis inhibitor is applied to the corneal pocket and the corneal pocket is routinely examined for neovascularization. See, e.g., Example 11 infra.

The therapeutically effective dosage for inhibition of angiogenesis in vivo, defined as inhibition of capillary endothelial cell proliferation, migration, and/or blood vessel ingrowth, may be extrapolated from in vitro inhibition assays using the compositions of the invention above or in combination with other angiogenesis inhibiting factors. The effective dosage is also dependent on the method and means of delivery. For example, in some applications, as in the treatment of psoriasis or diabetic retinopathy, the inhibitor is delivered in a topical-ophthalmic carrier. In other applications, as in the treatment of solid tumors, the inhibitor is delivered by means of a biodegradable, polymeric implant.

5.3. Therapeutic Uses

The invention provides for compositions and methods for inhibition of angiogenesis. The invention further provides for compositions and methods for treatment or prevention of diseases or disorders associated with neovascularization by administration of a therapeutic compound of the invention. Such compounds (termed herein "Therapeutics") include troponin subunits and fragments and homologs thereof (e.g., as described supra).

5.3.1. Malignancies

Malignant and metastatic conditions which can be treated with the Therapeutic compounds of the present invention include, but are not limited to, the solid tumors listed in Table 1 (for a review of such disorders, see Fishman et al., 1985, *Medicine,* 2d Ed., J. B. Lippincott Co., Philadelphia) and blood-borne tumors such as leukemias.

Table 1

Malignancies and Related Disorders

Solid tumors
  sarcomas and carcinomas
    fibrosarcoma
    myxosarcoma
    liposarcoma
    chondrosarcoma
    osteogenic sarcoma
    chordoma
    angiosarcoma
    endotheliosarcoma
    lymphangiosarcoma
    lymphangioendotheliosarcoma
    synovioma
    mesothelioma
    Ewing's tumor
    leiomyosarcoma
    rhabdomyosarcoma
    colon carcinoma
    pancreatic cancer
    breast cancer
    ovarian cancer
    prostate cancer
    squamous cell carcinoma
    basal cell carcinoma
    adenocarcinoma
    sweat gland carcinoma
    sebaceous gland carcinoma
    papillary carcinoma
    papillary adenocarcinomas
    cystadenocarcinoma
    medullary carcinoma
    bronchogenic carcinoma
    renal cell carcinoma
    hepatoma
    bile duct carcinoma
    choriocarcinoma
    seminoma
    embryonal carcinoma
    Wilms' tumor
    cervical cancer
    testicular tumor
    lung carcinoma
    small cell lung carcinoma
    bladder carcinoma
    epithelial carcinoma
    glioma
    astrocytoma
    medulloblastoma
    craniopharyngioma
    ependymoma
    Kaposi's sarcoma
    pinealoma
    hemangioblastoma
    acoustic neuroma
    oligodendroglioma
    menangioma
    melanoma
    neuroblastoma
    retinoblastoma

5.3.2. Ocular Disorders

Ocular disorders associated with neovascularization which can be treated with the Therapeutic compounds of the present invention include, but are not limited to:
  neovascular glaucoma
  diabetic retinopathy
  retinoblastoma
  retrolental fibroplasia
  uveitis
  retinopathy of prematurity
  macular degeneration
  corneal graft neovascularization
  as well as other eye inflammatory diseases, ocular tumors and diseases associated with choroidal or iris neovascularization. See, e.g., reviews by Waltman et al., 1978, *Am. J. Ophthal.* 85:704-710 and Gartner et al., 1978, *Surv. Ophthal.* 22:291-312.

5.3.3. Other Disorders

Other disorders which can be treated with the Therapeutic compounds of the present invention include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

5.4. Demonstration of Therapeutic or Prophylactic Utility

The Therapeutics of the invention can be tested in vivo for the desired therapeutic or prophylactic activity as well as for determination of therapeutically effective dosage. For example, such compounds can be tested in suitable animal model systems prior to testing in humans, including, but not limited to, rats, mice, chicken, cows, monkeys, rabbits, etc. For in vivo testing, prior to administration to humans, any animal model system known in the art may be used.

5.5. Therapeutic/Prophylactic Administration and Compositions

The invention provides methods of inhibition of angiogenesis and method of treatment (and prophylaxis) by administration to a subject an effective amount of a Therapeutic of the invention. In a preferred aspect, the Therapeutic is substantially purified as set forth in Examples 1 and 7. The subject is preferably an animal, including, but not limited to, animals such as cows, pigs, chickens, etc., and is more preferably a mammal, and most preferably a human.

The invention also provides for methods of treatment and prevention by administration of an effective amount of a Therapeutic of the invention to an immunocompromised patient, for example, a patient having cancer or infected with human immunodeficiency virus (HIV). In particular, the invention may be used to treat or prevent secondary infections or diseases associated with HIV infection or cancers.

The invention further provides methods of treatment and prevention by administration to a subject, an effective amount of a Therapeutic of the invention combined with a chemotherapeutic agent and/or radioactive isotope exposure.

The invention also provides for methods of treatment and prevention of a Therapeutic of the invention for patients who have entered a remission in order to maintain a dormant state.

Various delivery systems are known and can be used to administer a Therapeutic of the invention, e.g., encapsulation in liposomes, microparticles, microcapsules, receptor-mediated endocytosis (see, e.g., Wu and Wu, 1987, *J. Biol. Chem.* 262:4429-4432). Methods of introduction include, but are not limited to, topical, intradermal, intramuscular, intraperitoneal, intravenous, subcutaneous, intranasal, epidural, ophthalmic, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. It is preferred that administration is localized, but it may be systemic. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of a malignant tumor or neoplastic or pre-neoplastic tissue.

For topical application, the purified troponin subunit is combined with a carrier so that an effective dosage is delivered, based on the desired activity (i.e., ranging from an effective dosage, for example, of 1.0 μM to 1.0 mM to prevent localized angiogenesis, endothelial cell migration, and/or inhibition of capillary endothelial cell proliferation. In one embodiment, a topical troponin subunit, fragment or homolog is applied to the skin for treatment of diseases such as psoriasis. The carrier may in the form of, for example, and not by way of limitation, an ointment, cream, gel, paste, foam, aerosol, suppository, pad or gelled stick.

A topical Therapeutic for treatment of some of the eye disorders discussed infra consists of an effective amount of troponin subunit, fragment, or homolog, in a ophthalmologically acceptable excipient such as buffered saline, mineral oil, vegetable oils such as corn or arachis oil, petroleum jelly, Miglyol 182, alcohol solutions, or liposomes or liposome-like products. Any of these compositions may also include preservatives, antioxidants, antibiotics, immunosuppressants, and other biologically or pharmaceutically effective agents which do not exert a detrimental effect on the troponin subunit.

For directed internal topical applications, for example for treatment of ulcers or hemorrhoids, the troponin subunit, fragment, or homolog composition may be in the form of tablets or capsules, which can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; or a glidant such as colloidal silicon dioxide. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

Suppositories generally contain active ingredient in the range of 0.5% to 10% by weight; oral formulations preferably contain 10% to 95% active ingredient.

In another embodiment, the Therapeutic can be delivered in a vesicle, in particular a liposome. See, Langer et al., 1990, *Science* 249:1527-1533; Treat et al., 1989, in Liposomes in the Therapy of Infectious Disease and Cancer, Lopez-Berestein and Fidler (eds.), Liss, New York, pp. 353-365; Lopez-Berestein, ibid., pp. 317-327.

In yet another embodiment, the Therapeutic can be delivered in a controlled release system. In one embodiment, an infusion pump may be used to administer troponin subunit, such as for example, that used for delivering insulin or chemotherapy to specific organs or tumors (see Langer, supra; Sefton, *CRC Crit. Ref. Biomed.*, 1987, Eng. 14:201; Buchwald et al., 1980, *Surgery* 88:507; Saudek et al., 1989, *N. Engl. J. Med.* 321:574.

In a preferred form, the troponin subunit, fragment, or homolog is administered in combination with a biodegradable, biocompatible polymeric implant which releases the troponin subunit, fragment, or homolog over a controlled period of time at a selected site. Examples of preferred polymeric materials include polyanhydrides, polyorthoesters, polyglycolic acid, polylactic acid, polyethylene vinyl acetate, and copolymers and blends thereof. See, Medical Applications of Controlled Release, Langer and Wise (eds.), 1974, CRC Pres., Boca Raton, Fla.; Controlled Drug Bioavailability, Drug Product Design and Performance, Smolen and Ball (eds.), 1984, Wiley, New York; Ranger and Peppas, 1983, *J. Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105. In yet another embodiment, a controlled release system can be placed in proximity of the therapeutic target, i.e., the brain, thus requiring only a fraction of the systemic dose (see, e.g., Goodson, in Medical Applications of Controlled Release, 1989, supra, vol. 2, pp. 115-138).

Other controlled release systems are discussed in the review by Langer (1990, *Science* 249:1527-1533).

The present invention also provides pharmaceutical compositions. Such compositions comprise a therapeutically effective amount of a Therapeutic, and a pharmaceutically acceptable carrier.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier"

refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose are also envisioned. The parental preparation can be enclosed in ampoules, disposable syringes or multiple dose vials made of glass or plastic.

These compositions can take the form of solutions, suspensions, emulsion, tablets, pills, capsules, powders, sustained-release formulations and the like. The composition can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The amount of the Therapeutic of the invention which will be effective in the treatment of a particular disorder or condition will depend on the nature of the disorder or condition, and can be determined by standard clinical techniques. In addition, in vitro assays such as those discussed in section 5.2 may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration of full-length troponin subunits are generally about 20-500 micrograms of active compound per kilogram body weight. Suitable dosage ranges for intranasal administration of full-length troponin subunits are generally about 0.01 pg/kg body weight to 1 mg/kg body weight. Suitable dosage ranges for intravenous administration of troponin fragments are generally about 10 micrograms to 1 milligram of active compound per kilogram body weight, preferably about 150 milligrams per administration, more preferably about 120 milligrams per human. Effective doses may be extrapolated from dose-response curves derived from in vitro or animal model test bioassays or systems.

Administration of the doses. recited above can be repeated. In a preferred embodiment, the doses recited above are administered 2 to 7 times per week. The duration of treatment depends upon the patient's clinical progress and responsiveness to therapy.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Modifications and variations of the compositions of the present invention, and methods for use, will be obvious to those skilled in the art from the foregoing detailed description. Such modifications and variations are intended to fall within the scope of the appended claims.

The following non-limiting examples demonstrate the discovery of troponin subunit inhibition of angiogenic stimulus induced endothelial cell proliferation, and means for determining the effective dosage of troponin subunit, fragment, or homolog to inhibit angiogenesis, as well as for identifying troponin subunit fragments and homologs (i.e., those fragments or homologs of troponin subunit capable of inhibiting angiogenesis. The troponin subunit used in the examples is purified as described infra.

6. EXAMPLES

Example 1

Purification of Troponin Subunit Components

Cardiac Troponin Isolation from Tissue

The procedures of Ebashi et al., 1968, *J. Biochem.* 64:465-477; Yasui et al., 1968, *J. Biol. Chem.* 243:735-742; Hartshorne et al., 1969, *Biochim. Biophys. Acta,* 175:30; Schaub et al., 1969, *Biochem. J.* 115:993-1004; Greaser et al., 1971, *J. Biol. Chem.* 246:4226-4233; and Greaser et al., 1973, *J. Biol. Chem.* 248:2125-2133 for purifying troponin can be used. Rabbit back and leg muscles are removed, cleaned of fat and connective tissue, and ground. The ground muscle (1 kg) is stirred for 5 min. in 2 liters of a solution containing 20 mM KCl, 1 mM $KHCO_3$, 0.1 mM $CaCl_2$, and 0.1 mM DTT. The suspension is filtered through cheesecloth, and the washing of the residue is repeated four times. Two liters of 95% ethanol are then added to the washed residue and the solution filtered after 10 min. The ethanol extraction is repeated twice. The residue is then washed 3 times with 2 liters of diethyl ether for 10 min. Finally the residue is allowed to dry at room temperature for 2 to 3 hours.

[1]The abbreviations used are: DDT, dithiothreitol; EGTA, ethylene glycol bis (β-aminoethyl ether)-N,N'-tetraacetate; SDS, sodium dodecyl sulfate; SE-, sulfoethyl.

The dried powder (from 1 kg of muscle) is extracted overnight at 22° with 2 liters of a solution containing 1 M KCl, 25 mM Tris (pH 8.0), 0.1 mM CaCi$_2$, and 1 mM DTT. After filtration through cheesecloth, the residue is once more extracted with 1 liter of 1 M KCl.

The extracts are combined and cooled to 4° C. Solid ammonium sulfate is added to produce approximately 40% saturation (230 g per liter). After 30 min. the solution is centrifuged and 125 g of ammonium sulfate is then added per liter of supernatant (60% saturation). After centrifugation the precipitate is dissolved in 500 ml of a solution containing 5 mM Tris (pH 7.5), 0.1 mM CaCl$_2$, and 0.1 mM DTT and dialyzed against 15 liters of the same solution for 6 hours and against a fresh solution overnight.

Solid KCl is added to a final concentration of 1 M and 1 M KCl solution is added to bring the volume to 1 liter. The pH is then adjusted to 4.6 by addition of HCl, and the tropomyosin precipitate is removed by centrifugation. The pH of the supernatant is adjusted to 7.0 with KOH, and 450 g of ammonium sulfate are added per liter (70% saturation). The precipitate is dissolved in a solution containing 5 mM Tris (pH 7.5, 0.1 mM CaCl$_2$, and 0.1 mM DTT, and dialyzed overnight against the same solution. Solid KCl is added to bring its concentration to 1 M, the pH adjusted to 4.6, and the precipitate which forms is removed by centrifugation. The neutralized supernatant is dialyzed against 2 mM Tris (pH 7.5) until the Nessler reaction is negative. The final yield of troponin is usually 2.5 to 3.0 g per kg of fresh muscle.

Cardiac Troponin Isolation from Tissue

Bovine hearts are obtained approximately 30 min. after death and immediately cut open, rinsed of blood, and immersed in ice. The left ventricle is removed, trimmed of excess fat and connective tissue, and ground. All subsequent extraction and preparation steps are performed at 0-3° except where noted. The ground muscle (500 g) is homogenized in a Waring Blender for 1 min. in 2.5 liters of solution containing 0.09 M KH$_2$PO$_4$, 0.06 M K$_2$HPO$_4$, 0.3 M KCl, 5 mM 2-mercaptoethanol, pH 6.8. The homogenized muscle suspension is then stirred for 30 min. and centrifuged at 1000×g for 20 min. The precipitate is re-extracted for 30 min. and centrifuged. The residue is then washed with 2.5 liters of 5 mM 2-mercaptoethanol and centrifuged at 1000×g for 10 min., followed by two successive washings and centrifugations with 1.5 liters of 50 mM KCl, 5 mM Tris-HCl (pH 8.1), and 5 mM 2-mercaptoethanol. The residue is then washed and centrifuged twice with 1.5 liters of 50 mM Tris-HCl (pH 8.1), and 5 mM 2-mercaptoethanol. The volume of the residue is measured, and the residue is mixed with 0.5 volume of 3 M KCl, 50 mM Tris-HCl (pH 8.1), and 5 mM 2-mercaptoethanol. After a 16- to 20-hour extraction at 0°, the suspension is centrifuged at 15,000×g for 10 min. The sediment is discarded, and the supernatant is adjusted to pH 7.6 with 0.05 N HCl. The filamentous precipitate which forms upon pH adjustment is removed by filtering the extract through nylon gauze. The protein that precipitates between 30 and 50% ammonium sulfate saturation is collected, dissolved in a solution containing 1 M KCl, and 1 mM potassium phosphate (pH 6.8), and 5 mM 2-mercaptoethanol, and dialyzed against the same solution for 4 hours and against a fresh solution overnight. The protein solution is clarified by centrifugation at 105,000×g for 30 min. The troponin is then purified by chromatography on a hydroxylapatite column with the protein being eluted between 0.08 and 0.10 M phosphate. Greaser et al., 1972 *Cold Spring Harbor Symp. Quant. Biol.* 37:235-244. Rabbit cardiac troponin is prepared in a similar manner using a pooled batch of hearts which has been stored at −20° C. prior to extraction.

The troponin subunits are separated by DEAE-Sephadex chromatography in 6 M urea. Bovine cardiac tropomyosin is prepared from the 50% ammonium sulfate saturation supernatant from the troponin extraction scheme (see above). Ammonium sulfate is added to 65% saturation, and the precipitate is dissolved in and dialyzed versus 1 M KCl, 1 mM potassium phosphate (pH 7.0), and 5 mM 2-mercaptoethanol. The protein is then purified by hydroxylapatite chromatography.

Protein Determination

Protein concentrations are determined by the biuret method of Gornall et al. using bovine serum albumin as a standard. Gornall et al., 1949, *J. Biol. Chem.*, 177:751-766.

Separation of Components

A sequence of SP-Sephadex and DEAE-Sephadex chromatography gives complete separation of the three cardiac troponin components.

Recombinant Troponin Isolation and Reconstitution Protocols Troponin I and T

DNA encoding various troponin subunits and isoforms are known in the art. See, e.g., Wu et al., 1994, *DNA Cell. Biol.* 13:217-233; Schreier et al., 1990, *J. Biol. Chem.* 265:21247-21253; and Gahlmann et al., 1990, *J. Biol. Chem.* 265:12520-12528.

To express a troponin subunit, DNA encoding the subunit is subcloned into a high copy number expression plasmid, such as KP3998, using recombinant techniques known in the art.

To express the cloned cDNA, *E. coli* transformed with the insert-containing pKP1500 vector is grown overnight at 37° C., then inoculated into 4 liters of Luria-Bertani broth (LB) medium and grown at 42° C. until mid-log phase. Isopropyl-1-thio-β-D-gal-actopyranoside is then added to 0.5 mM, and the culture is allowed to grow at 42° C. overnight. Purification of expressed troponin subunit, fragment, or homolog may be adapted from published procedures (Reinach et al., 1988, *J. Biol. Chem.* 250:4628-4633 and Xu et al., 1988, *J. Biol. Chem.* 263:13962-13969). The cells are harvested by centrifugation and suspended in 20 ml of 20 mM Tris, 20% sucrose, 1 mM EDTA, 0.2 mM phenylmethylsulfonyl fluoride, 1 mg/ml lysozyme, pH 7.5. After incubation on ice for 30 min., 80 ml of 20 mM Tris, 1 mM EDTA, 0.2 mM phenylmethylsulfonyl fluoride, 0.5 mm DTT is added and the cells broken in a French press (SLM Instruments). The cell debris is pelleted; the supernatant is made 35% in saturated (NH$_4$)$_2$SO$_4$ and stirred on ice for 30 min. After sedimentation, the supernatant is made 50 mM in NaCl, 5 mM in CaCl$_2$, 1 mM in MgCl$_2$, and 1 mM in DTT and then loaded onto a 1.5×25-cm phenyl-Sepharose (Pharmacia LKB Biotechnology Inc.) column. The column is washed first with 50 mM Tris, 50 mM NaCl, 5 mM CaCl$_2$, 1 mM MgCl$_2$, 1 mM DTT, pH 7.5, then with 50 mM Tris, 1 mM NaCl, 0.1 mM CaCl$_2$, 1 mM DTT, pH 7.5, until no more protein is eluted. The crude troponin subunit is then eluted with 50 mM Tris, 1 mM EDTA, 1 mM DTT, pH 7.5. Fractions that contain troponin subunit, fragment, or homolog are pooled, dialyzed against 25 mM Tris, 6 M urea (United States Biochemical Corp.), 1 mM MgCl$_2$, 1 mM DTT, pH 8.0, and loaded onto a 1.5×25-cm DE52 (Whatman) column. The column is eluted with a 0-0.6 M NaCl linear gradient. Troponin subunit, fragment, or homolog which elutes from the column is dialyzed against 0.1 mM $NH_4HCO_3$, 1 mM β-mercaptoethanol, lyophilized, and stored. Purity is assessed by SDS-polyacrylamide gel electrophoresis and UV spectrophotometry. Typical yields of 6 mg of purified recombinant troponin subunit, fragment, or homolog/liter of bacterial culture are expected.

The lyophilized recombinant protein is resuspended in a take up buffer consisting of 6M urea, 20 mM Hepes (pH 7.5), 0.5M NaCl, 2 mM EDTA, and 5 mM DTT. The mixture is nutated at room temperature for 1 hour. The solution is then dialyzed at 4° C. for six hours with 1 exchange against a dialysis buffer consisting of 0.5 M NaCl, 20 mM Hepes (pH 7.5), and 0.5mM DTT.

Protein concentration is determined for each subunit at 280λ. The extension coefficient of Troponin I is 0.40 and Troponin T is 0.50.

Troponin C

The lyophilized recombinant protein is resuspended in a take up buffer consisting of 0.1 M NaCl, 20 mM Hepes (pH 7.5), 2 mM EDTA, and 5 mM DTT. This solution is dialyzed for 6 hours at 4° C. with one exchange against a dialysis buffer of 0.1 M NaCl, 20 mM Hepes (pH 7.5), and 0.5 mM DTT.

Protein concentration is determined by measuring absorbance at 280λ. The extension coefficient for troponin C is 0.18.

Reconstitution of Combined Subunits

Protein concentrations having the same reconstitution molar ratios of troponin subunits C, I, and T are maintained for all various combinations. These concentrations of the respective proteins are combined in a reconstitution buffer consisting of 0.1 M NaCl, 0.1 M CaCl2, 5 mM DTT, 5 mM Hepes (pH 7.5). Dialysis is for 20-24 hours at 4° C. with three exchanges over a dialysis buffer consisting of 0.1 M NaCl, 0.1 m $CaCl_{2,\ 0.5}$ mM DTT, and 5 mM Hepes (pH 7.5).

Protein concentration is approximated by measuring absorption at 278λ. The troponin trimer has an extension coefficient of 0.45 at 278λ.

Example 2

Inhibition of Endothelial Cell Proliferation Measured by DNA Synthesis

The inhibitory effect of troponin subunit, fragment, or homolog on the proliferation of bFGF-stimulated EC can be measured according to the following procedure.

Endothelial Cell DNA Synthesis

On day one, 5,000 bovine capillary endothelial cells in DMEM/10% CS/1% GPS are plated onto each well of a 96-well pregelatinized tissue culture plate. On day two, the cell media is changed to DMEM, 2% CS, 1% GPS, 0.5% BSA (complete medium), supplemented with 10 µl of 1 mg/ml "cold" thymidine per 50 ml of medium. On day three, test samples in complete medium are added in duplicate. Additionally, beta Fibroblast Growth Factor (bFGF) is added to each well except for the appropriate controls, to a final concentration of 0.2 ng/well. On day four, 5 µl of 1:13 diluted $^3$H-Thymidine stock is added to each well and the plate is incubated for 5-6 hours. Following incubation, the medium is aspirated, and the remainder is rinsed once with PBS, then twice for 5 minutes each with methanol followed by two rinses each for 10 minutes with 5% TCA. The cells are then rinsed with water three times, dried to the plate, and 100 µl of 0.3 N NaOH is added to each well. The contents of the well are then transferred to the scintillation counter vials and 3 mls of Ecolume added to each vial. Samples are then counted on the scintillation counter.

3T3 Cell DNA Synthesis

DNA synthesis in bFGF-stimulated 3T3 cells provides a control with which to evaluate results obtained for bFGF stimulated endothelial cell proliferation. DNA synthesis in the 3T3 cells can be determined according to the following method.

BALB/c 3T3 cells are trypsinized and resuspended at a concentration of $5×10^4$ cells/ml. Aliquots of 200 µl are plated into 0.3 cm$^2$ microtiter wells (Microtest II tissue Culture Plates, Falcon). After reaching confluence, in a period of 2 to 3 days, the cells are further incubated for a minimum of 5 days in order to deplete the media of growth promoting factors. These growth conditions yield confluent monolayers of non-dividing BALB/c 3T3 cells. Test samples are dissolved in 50 µl of 0.15 M NaCl and added to microtiter wells, along with [$^3$H]TdR. After an incubation of at least 24 hours, the media is removed and the cells are washed in PBS. Fixation of the cells and removal of unincorporated [$^3$H]TdR is accomplished by the following successive steps; addition of methanol twice for periods of 5 minutes, 4 washes with $H_2O$, addition of cold 5% TCA twice for periods of 10 minutes, and 4 washes with $H_2O$. DNA synthesis is measured either by liquid scintillation counting or by autoradiography using a modification of the method described by Haudenschild et al., 1976, *M. Exp. Cell Res.* 98:175. For scintillation counting, cells are lysed in 150 µl of 0.3 N NaOH and counted in 5 ml of Insta-Gel liquid scintillation cocktail (Packard) using a Packard Tri-Carb liquid scintillation counter. Alternatively, autoradiography may be used to quantitate DNA synthesis by punching out the bottoms of the microtiter wells and mounting them on glass slides with silastic glue. The slides are dipped in a 1 g/ml solution of NTB2 nuclear track emulsion (Kodak) and exposed for 3-4 days. The emulsion is developed with Microdol-X solution (Kodak) for 10 minutes, rinsed with distilled $H_2O$, and fixed with Rapid Fixer (Kodak) for three minutes. The autoradiographs are stained with a modified Giemsa stain. At least 1000 nuclei are counted in each well and DNA synthesis, expressed as the percentage of nuclei labeled. Cell division is measured by counting the number of cells in microtiter wells with the aid of a grid after 40-48 hour incubations with test samples.

Example 3

Inhibition of Endothelial Cell Proliferation Measured by Calorimetric Determination of Cellular Acid Phosphatase Activity and Electronic Cell Counting A quick and sensitive screen for inhibition of EC proliferation in response to treatment with a troponin subunit, homolog, or derivative of the invention involves incubating the cells in the presence of varying concentrations of the inhibitor and determining the number of endothelial cells in culture based on the colorimetric determination of cellular acid phosphatase activity, described by Connolly, et al., 1986, *J. Anal. Biochem.* 152:136-140.

The effect of troponin on the proliferation of capillary endothelial cells (EC) was measured in an assay which measures the ability of this protein to interfere with stimulation of endothelial cell proliferation by a known angiogenesis factor (bFGF).

Capillary endothelial cells and Balb/c 3T3 cells were separately plated ($2\times10^3/0.2$ ml) onto gelatin-coated 96-well tissue culture dishes on day 1. On day 2, cells were refed with Dulbecco's modified Eagle's medium (Gibco) with 5% calf serum (Hyclone) (DMEM/5) and bFGF (10 ng/ml) (FGF Co.) and increasing concentrations of one or more troponin subunits. These substances were added simultaneously in volumes that did not exceed 10% of the final volume. Wells containing phosphate buffered saline (PBS) (Gibco) alone and PBS+bFGF were included as controls. On day 5, media was removed and cells were washed with PBS and lysed in 100 µl of buffer containing 0.1 M sodium acetate (pH 5.5), 0.1% Triton X-100™ and 100 mM p-nitrophenyl phosphate (Sigma 104 phosphatase substrate). After incubation for 2 hours at 37° C., the reaction was stopped with the addition of 10 µl of 1 N NAOH. Color development was determined at 405 nm using a rapid microplate reader (Bio-Tek).

Percent inhibition was determined by comparing the cell number of wells exposed to stimulus with those exposed to stimulus and troponin subunits.

All three troponin subunits were found to inhibit bFGF-stimulated EC proliferation, as measured by the colorimetric assay.

Troponin C inhibited bFGF-stimulated endothelial cell proliferation in a dose-dependent manner in all concentrations tested (FIG. 1). Percent inhibition of bovine endothelial cell proliferation ("BCE") was 54%, 86%, 83%, and 100% at concentrations of 280 nM, 1.4 µM, 2.8 µM and 5.6 µM, respectively. An inhibition of 100% was observed at a concentration of 20 µg/well (5.6 µM). $IC_{50}$ represents the concentration at which 50% inhibition of bFGF growth factor-induced stimulation was observed. The $IC_{50}$ of troponin C was determined to be 278 nM.

Figure 2:
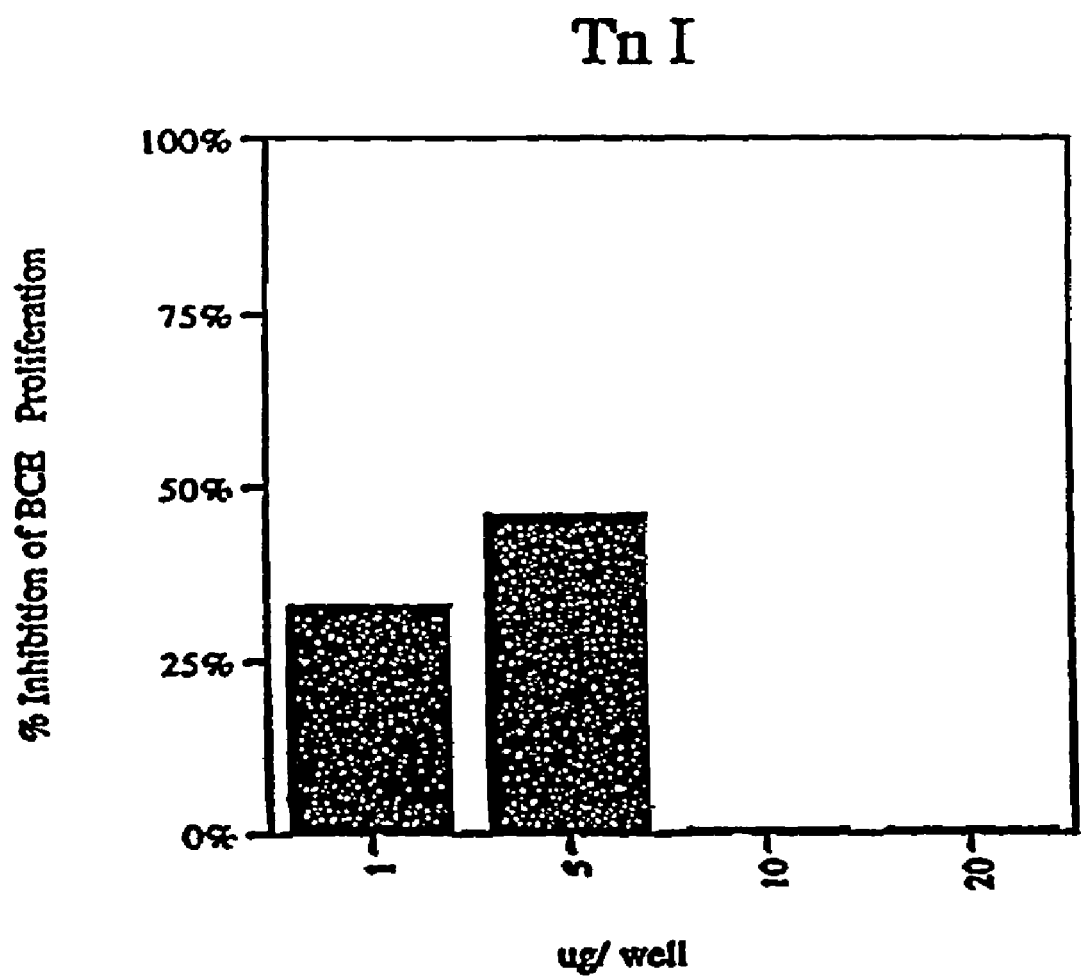

Troponin I inhibited bFGF-stimulated BCE proliferation at concentrations of 1 and 5 µg/well, but inhibition was not observed in the sample tested at 10 µg/well (FIG. 2). The percent inhibition of BCE was 33% and 46% at concentrations of 240 nM and 1.2 µM, respectively. The $IC_{50}$ of troponin I was determined to be 1.14 µM.

Figure 3:
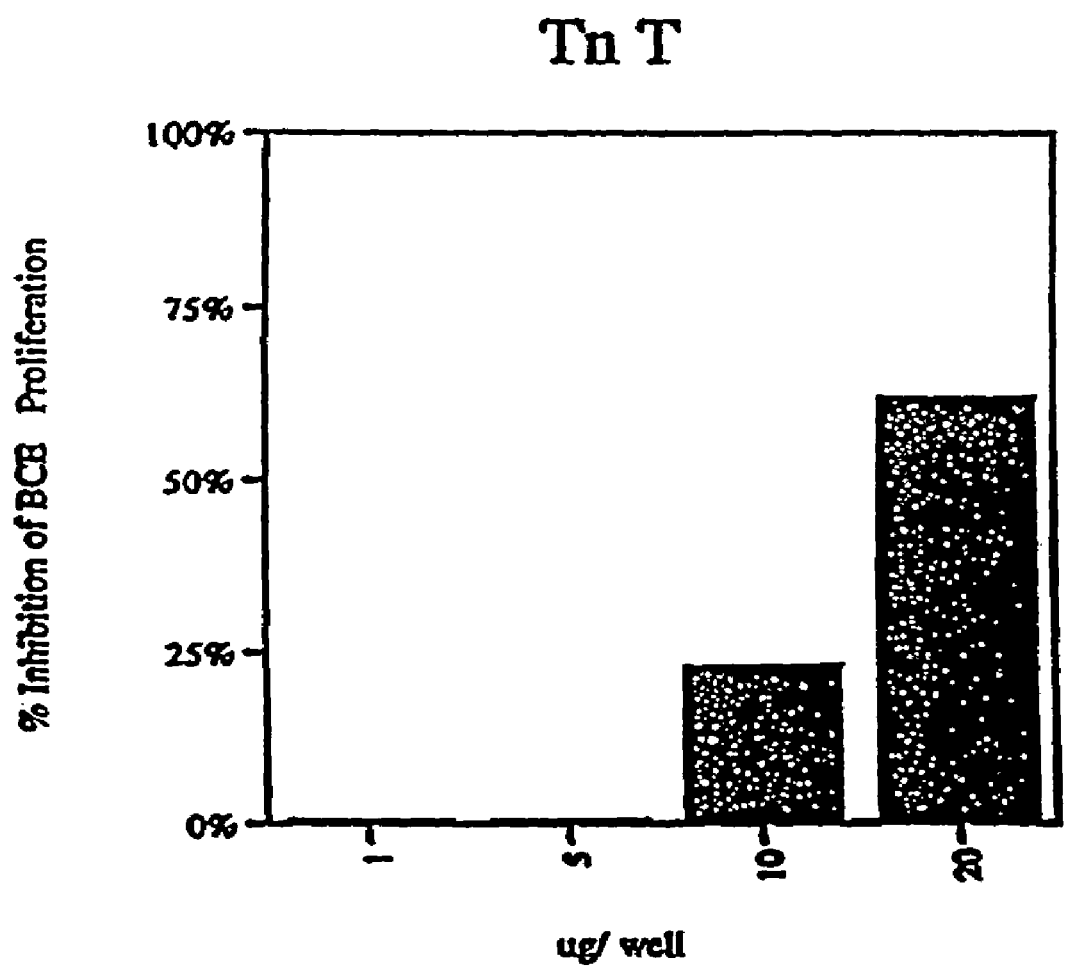

Troponin T inhibited bFGF-stimulated EC proliferation at concentrations of 10 and 20 µg/well, but not at concentrations of 1 and 5 µg/well (FIG. 3). BCE proliferation was inhibited 23% and 62% at 1.6 µM and 3.3 µM, respectively. The $IC_{50}$ of troponin T was determined to be 2.14 µM.

Figure 4:
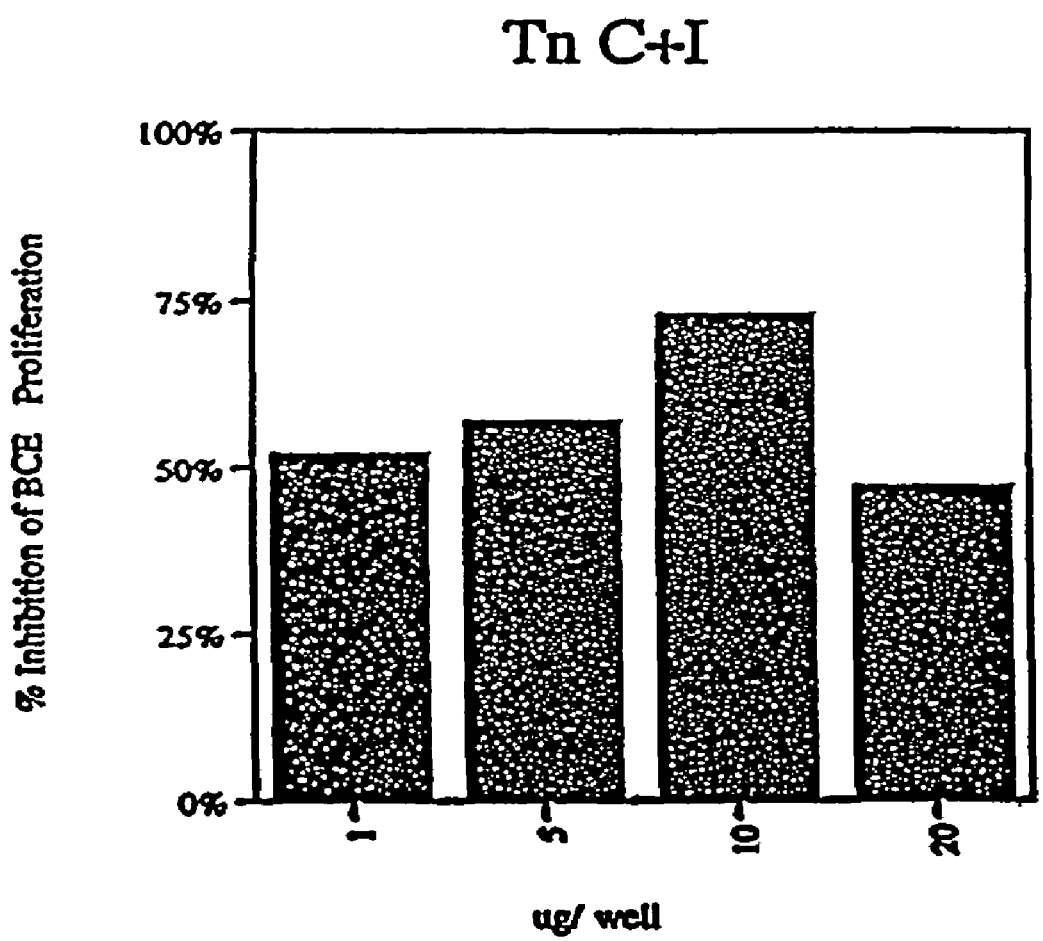

The combination of troponin subunits C and I inhibited EC at all concentrations tested (FIG. 4). The percent inhibition of proliferation of BCE was 52%, 54% 73% and 47% at 130 nM, 645 nM, 1.3 µM and 2.6 µM, respectively. The $IC_{50}$ of this combination was determined to be 110 nM.

Figure 5:
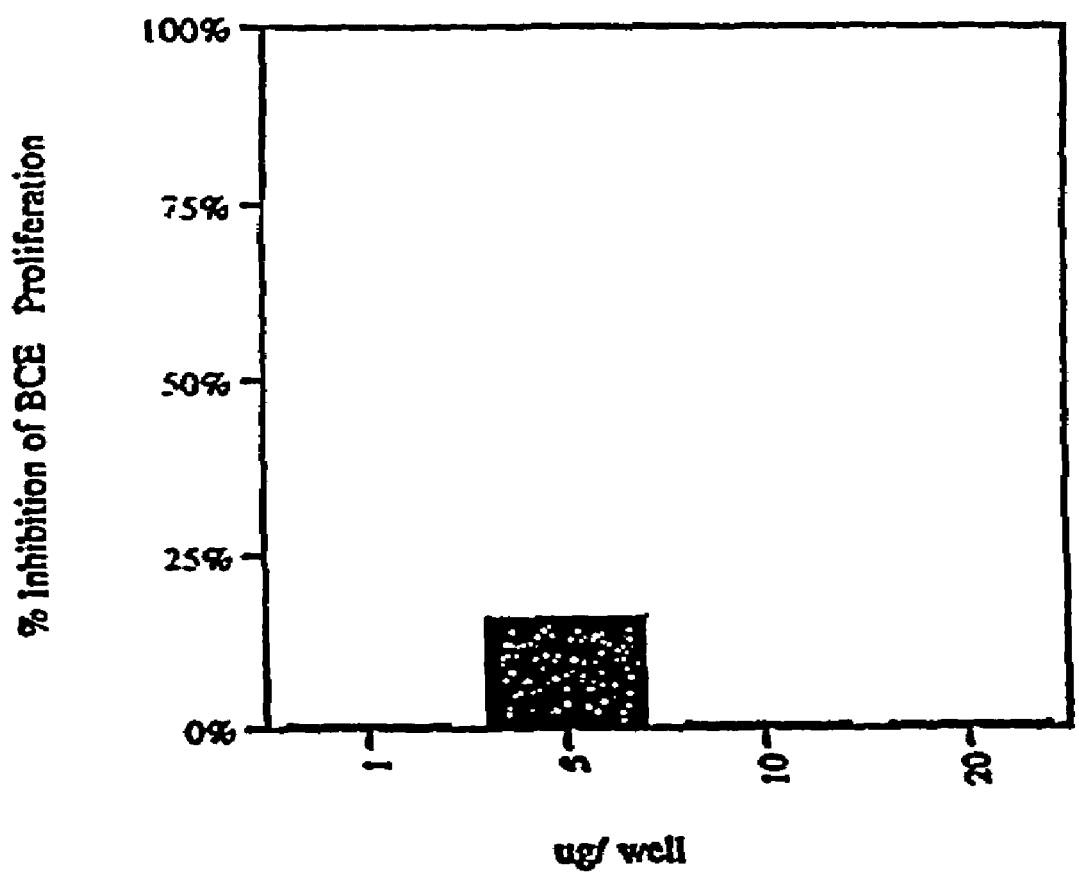

The combination of troponin subunits C, I and T was observed to inhibit bFGF-stimulated BCE proliferation by 16% at a concentration of 360 nM (5 µg/well, FIG. 5).

The troponin samples tested had no detectable inhibitory effect on the growth of Balb/c 3T3 cells, a non-endothelial cell type.

Example 4

Inhibition of Capillary Endothelial Cell Migration by Troponin

Determination of the ability of the troponin Subunit, fragment, or homolog to inhibit the angiogenic process of capillary EC migration in response to an angiogenic stimulus, can be determined using a modification of the Boyden chamber technique is used to study the effect of troponin subunit, fragment, or homolog on capillary EC migration. Falk et al., 1980, *J. Immunol.* 118:239-247 (1980). A blind-well Boyden chamber, consists of two wells (upper and lower) separated by a porous membrane. *J. Exp. Med.* 115:453-456 (1962). A known concentration of growth factor is placed in the lower wells and a predetermined number of cells and troponin subunit, fragment, or homolog is placed in the upper wells. Cells attach to the upper surface of the membrane, migrate through and attach to the lower membrane surface. The membrane can then be fixed and stained for counting, using the method of Glaser et al., 1980, *Nature* 288:483-484.

Migration is measured using blind well chambers (Neuroprobe, no. 025-187) and polycarbonate membranes with 8 micron pores (Nucleopore) precoated with fibronectin (6.67 µg/ml in PBS) (human, Cooper). Basic FGF (Takeda Co.) diluted in DMEM with 1% calf serum (DMEM/1) is added to the lower well at a concentration of 10 ng/ml. The upper wells receive $5\times10^5$ capillary EC/ml and increasing concentrations of purified troponin subunit, fragment or homolog is used within 24 hours of purification. Control wells receive DMEM/1, either with or without bFGF. The migration chambers are incubated at 37° C. in 10% $CO_2$ for 4 hours. The cells on the upper surface of the membrane are then wiped off by drawing the membrane over a wiper blade (Neuroprobe). The cells which have migrated through the membrane onto the lower surface are fixed in 2% glutaraldehyde followed by methanol (4° C.) and stained with hematoxylin. Migration is quantified by counting the number of cells on the lower surface in 16 oil immersion fields and comparing this number with that obtained for the control.

Example 5

Inhibition In Vivo of Neovascularization by Troponin as Determined by the Chick Chorioallantoic Membrane Assay The chick chorioallantoic membrane assay (CAM), may be used to determine whether troponin subunit, fragment or homolog is capable of inhibiting neovascularization in vivo. Taylor and Folkman, 1982, *Nature* (London) 297:307-312. The effect of troponin subunit, fragment or homolog on growing embryonic vessels is studied using chick embryos in which capillaries appear in the yolk sac at 48 h and grow rapidly over the next 6-8 days.

Three day post fertilization chick embryos are removed from their shells and placed in plastic petri dishes (1005, Falcon). The specimens are maintained in humidified 5% $CO_2$ at 37° C. On day 6 of development, samples of purified troponin subunit, fragment or homolog are mixed in methylcellulose disks and applied to the surfaces of the growing CAMs above the dense subectodermal plexus. Control specimens in which CAMs are implanted with empty methylcellulose disks are also prepared. The CAMs are injected intravascularly with India ink/Liposyn to more clearly delineate CAM vascularity. Taylor et al., 1982, *Nature* 297:307-312.

Following a 48 hour exposure of the CAMs to the troponin subunit, fragment, or homolog, the area around the implant is observed and evaluated. Test specimens having avascular zones completely free of India-ink filled capillaries surrounding the test implant indicate the presence of an inhibitor of embryonic neovascularization. In contrast, the control specimens show neovascularization in close proximity or in contact with the methylcellulose disks.

Histological mesodermal studies are performed on the CAMs of test and control specimens. The specimens are embedded in JB-4 plastic (Polysciences) at 4° C. and 3 μm sections are cut using a Reichert 2050 microtome. Sections are stained with toluidine blue and micrographs are taken on a Zeiss photomicroscope using Kodak TM ×100 and a green filter.

Example 6

Inhibition In Vivo of Neovascularization by Troponin as Determined by the Rabbit Corneal Packet Assay Male NZW rabbits weighing 4-5 lbs. are anesthetized with intravenous pentobarbital (25 mg/kg) and 2% xylocaine solution is applied to the cornea. The eye is proptosed and rinsed intermittently with Ringer's solution to prevent drying. The adult rabbit cornea has a diameter of approximately 12 mm. An intracorneal pocket is made by an incision approximately 0.15 mm deep and 1.5 mm long in the center of the cornea with a No. 11 scalpel blade, using aseptic technique. A 5 mm-long pocket is formed within the corneal stroma by inserting a 1.5 mm wide, malleable iris spatula. In the majority of animals, the end of the corneal pocket is extended to within 1 mm of the corneal-scleral junction. In a smaller series of 22 rabbits implanted with tumor alone, pockets are placed at greater distances—2-6 mm from the corneal-scleral junction by starting the incision away from the center.

In the first assay, polymer pellets of ethylene vinyl acetate (EVAc) copolymer are impregnated with test substance and surgically implanted in a pocket in the rabbit cornea approximately 1 mm from the limbus. When this assay system is being used to test for angiogenesis inhibitors, either a piece of V2 carcinoma or some other angiogenic stimulant is implanted distal to the polymer, 2 mm from the limbus. On the opposite eye of each rabbit, control polymer pellets that are empty are implanted next to an angiogenic stimulant in the same way. In these control corneas, capillary blood vessels start growing towards the tumor implant in 5-6 days, eventually sweeping over the blank polymer. In test corneas, the directional growth of new capillaries from the limbal blood vessels towards the tumor occurs at a reduced rate and is often inhibited such that an avascular region around the polymer is observed (FIG. 1). This assay is quantitated by measurement of the maximum vessel lengths with a stereoscopic microscope.

Example 7

Isolation of Troponin I from Cartilage

Purification of Troponin I from Cartilage

Troponin I was purified from bovine veal scapulae using a modification of a protocol previously described by us (Moses, et al., 1990, *Science* 2488, 1408-1410). Briefly, veal scapulae were vacuum frozen immediately after slaughter and stored at −20° C. until used. Cartilage was scraped first with a periosteal elevator (Arista) and then with a scalpel blade (No. 10, Bard-Parker) until clean of all muscle and connective tissue. Cartilage slices were extracted in 2 M NaCl, precipitated with HCl and ammonium sulfate (25-20%), and fractionated using a series of chromatography steps: gel filtration on A-1.5 m Sepharose (Bio-Rad) in the presence of 4M guanidine-HCl, ion exchange on a Bio-Rex 70 (Bio-Rad) cation exchange column, gel filtration on a Sephadex G-75 (superfine) (Pharmacia) column, reversed-phase high-performance liquid chromatography (HPLC) on a Hi-Pore 304 column (Bio-Rad) and gel filtration on a Progel-TSK G3000SWXL column (3.0 cm×7.8 mm) (Supelco). Fractions obtained from each column step were tested for their ability to inhibit capillary endothelial cell (EC) proliferation which was stimulated by basic Fibroblast Growth Factor (bFGF) as described below. Fractions containing inhibitory activity were pooled and concentrated in a Savant Speed Vac concentrator for amino acid and sequence analysis. Unless otherwise stated, all reagents were obtained from Sigma.

Trypsin Digestion, HPLC Separation and Microsequencing

Proteins were each reduced, S-carboxyamidomethylated and subjected to digestion with trypsin. The resulting peptide mixtures were fractionated by narrow bore high performance liquid chromatography using a Zorbax C18 1.0 mm by 150 mm reverse-phase column on a Hewlett-Packard 1090 HPLC with a 1040 diode array detector. Optimum fractions were chosen based on differential UV absorbance at 205, 277 nm and 292 nm, peak symmetry and resolution (Lane, et al., 1991, *J. Prot; Chem.* 10, 151-160). These fractions were then further screened for length and homogeneity by matrix-assisted laser desorption time-of-flight mass spectrometry (MALDI-TOF/MS) on a Thermo Bioanalysis Lasermat 2000 (Hemel, England). Tryptic peptide sequences were determined by electrospray ionization/tandem mass spectrometry on a Finnigan TSQ7000 (San Jose, Calif.) triple quadrupole mass spectrometer as described in Nash et al. (Nash, et al., 1996, *Curr; Biol.* 6, 968-980). Alternatively, peptides were submitted to automated Edman degradation on a PE/ABD 477A (Foster City, Calif.) protein sequencer.

Cloning and Expression of Human Troponin I

Human intercostal cartilage tissue was obtained according to bioethical guidelines pertaining to discarded clinical material. The cDNA encoding a fragment of human fast-twitch skeletal muscle troponin I was amplified by standard reverse transcriptase polymerase chain reaction (RT-PCR) from the total RNA isolated from a core sample of human cartilage using primers based on the nucleotide sequence of human fast-twitch skeletal muscle TnI (Zhu, et al., 1994, *Biochim. Biophys. Acta* 1217, 338-340): forward primer 5'-GCTCTG-CAAACAGCTGCACGCCAAG-3' (SEQ ID NO:4) and reverse primer 5,-GCCCAGCAGGGCCTTGAGCATG-GCA-3' (SEQ ID NO:5) which was cloned into PCR2.1 (Invitrogen) and sequenced in both directions. The cDNA encoding the full-length open reading frame (ORF) of human fast-twitch skeletal muscle troponin I was cloned from human skeletal muscle mRNA with Pfu polymerase (Stratagene) under standard PCR conditions, using forward primer (5'-CTCACCATGGGAGATGAGGAGAAGC-3') (SEQ ID NO:6) and the reverse primer (5'-GCCTCGAGTGGCCTAG-GACTCGGAC-3') (SEQ ID NO:7). The PCR product was cloned into the expression vector Pet24d (Novagen) using 5'-NcoI and 3'-XhoI sites and sequenced as above.

Tissue expression of TnI was analyzed by RT-PCR as described above. Total RNA (400 ng/sample) was isolated from rat skeletal muscle, liver (Clontech), xyphoid and Swarm rat chondrosarcoma. The design of the forward (5'-GAACACTGCCCGCCTCTGCACATC-3') (SEQ ID NO:8) and reverse (5'-GAGCCCAGCAGCGCCTTCAGCATG-3') (SEQ ID NO:9) primers was based on the nucleotide sequence of rat fast-twitch skeletal muscle TnI.

Recombinant(r) human TnI was expressed according to standard protocols (Sambrook, et al., 1989, *Molecular Cloning: A laboratory manual.* (Cold Spring Harbor Press, New York, N.Y.)). After 5 hrs of expression, bacteria were harvested by centrifugation. Following centrifugation at 12,000×g for 15 min, the pellet was resuspended in 1.0 ml of Buffer A (15 mM Tris-HCl, 0.1 mM EDTA, pH 7.0). The cells were disrupted by sonication. The inclusion bodies were isolated by centrifugation at 12,000×g once for 15 min in Buffer A, followed by centrifugation once at 11,000×g once for 15 min in Buffer A.

Purification of Recombinant Troponin I

The washed pellet was dissolved in 6 M urea, 0.5 M NaCl, 5 mM HEPES, 2 mM EDTA, 5 mM DTT (pH 7.5), and nutated in the above buffer for 6-8 hours at 4° C. The sample was then dialyzed against 0.5 M NaCl, 5 mM HEPES, 5 mM DTT (pH 7.5) and concentrated using an Amicon concentrator (YM-10, MWCO 10,000 Da) prior to application to a Progel-TSK G3000SWXL column (30 cm×7.8 mm). The sample was eluted using the above buffer (0.5 M NaCl, 5 mM HEPES, 5 mM DTT, pH 7.5). Some of the inhibitory preparations were further fractionated on a Q-Sepharose HP column (Pharmacia Biotech) and tested as described below with no difference in biological activity. Purified rTnI was dialyzed against phosphate buffered saline (PBS) containing 0.5 mM DTT prior to testing. Protein concentration was determined by scanning densitometric comparison (IS-1000 Digital Imaging System, Version 2.00, Alpha Innotech Corp.) with known protein standards (Novex) coelectrophoresed on sodium dodecyl sulfate polyacrylamide gel electrophoresis (SDS-PAGE) followed by staining with Coomassie Blue.

Western Blot Analysis

Immunoblotting was conducted on samples of native TnI (purified from cartilage as described above), recombinant TnI (purified as described above) and bovine chondrocyte lysates prepared as described below according to standard protocols. Cultures of primary bovine scapular chondrocytes were established and maintained as previously described by us (Moses, et al., 1990, *J. Cell. Biol.* 119, 474-481). Cells were rinsed with PBS and to each 10 cm culture dish was added 1 ml of boiling 2×-concentrated electrophoresis sample buffer (250 mM Tris-HCl, pH 6.8, 4% SDS, 10% glycerol, 0.006% bromophenol blue and 2% B-mercaptoethanol). Cells were scraped from the dishes using a disposable cell scraper (Costar), transferred to a microcentrifuge tube and boiled for an additional 5 min. Following several passages though a 26 gauge needle (Becton Dickinson), the sample was clarified by centrifugation (2000×g), diluted to 0.1% SDS, and the protein concentration determined using a DO Protein Assay (Bio-Rad). All samples were separated by polyacrylamide gel electrophoresis on a 4/12% acrylamide mini-gel according to Laemmli (Laemmli, 1970, *Nature* 227, 680-685). Proteins were then transferred to nitrocellulose (Hybond-ECL, Amersham) using a Transblot apparatus (Biorad),incubated with a monoclonal antibody to rabbit skeletal muscle TnI (Advanced Immunochemical Inc.) and developed using the ECL western blotting system according to the manufacturer's protocol (Amersham).

Results

Figure 6:
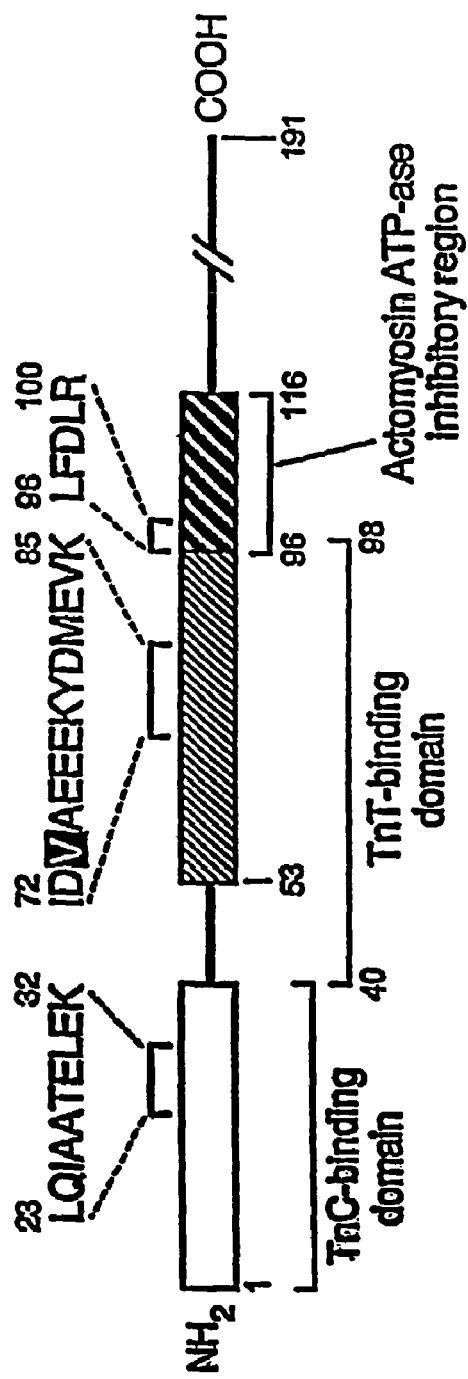

An in vitro assay which measures the inhibition of basic fibroblast growth factor (bFGF)-stimulated proliferation of capillary endothelial cells (EC) was used to monitor purification (Moses, et al., 1990, *Science* 2488, 1408-1410; Moses, et al., 1990, *J. Cell. Biol.* 119, 474-481; Connolly, et al., 1986, *Anal. Biochem.* 152, 136-140). All cartilage-derived fractions obtained from a series of chromatography steps described below were screened for this inhibitory bioactivity. Inhibitory activity eluted at an approximate molecular weight of 25,000 Da from the A-1.5 m-size exclusion column, at approximately 0.2M NaCl from the Biorex 70 cation exchange column, at approximately 23,000 Da from the Sephadex G-75 gel filtration column, at an acetonitrile concentration of approximately 38.5%, and at an approximate Mr of 22,000 Da from the Progel-TSK G3000SWXL column. Inhibitory fractions obtained from the final chromatography step were subjected to tryptic digestion and the resultant peptides were sequenced by microcapillary LC-ESI tandem mass spectrometry or automated Edman degradation. The sequences of three peptide fragments (LQIAATELEK, (SEQ ID NO:18; IDVAEEEKYDMEVK, (SEQ ID NO:19); AND LFDLR, (SEQ ID NO:20)) were obtained and were identified as fragments of troponin I (FIG. 6).

Figure 7A:
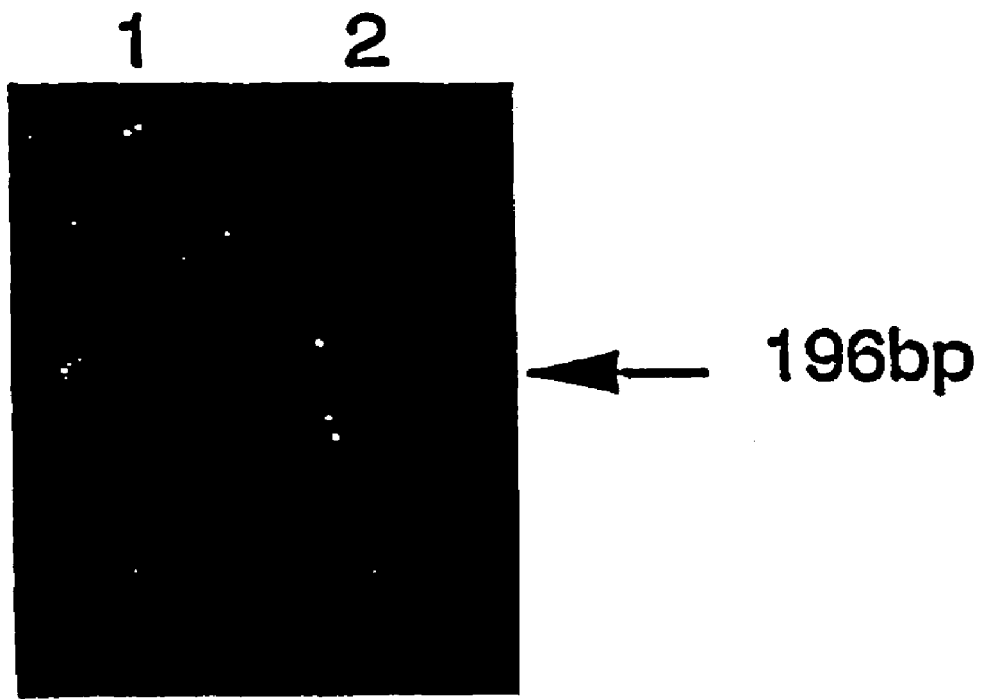
Figure 7C:
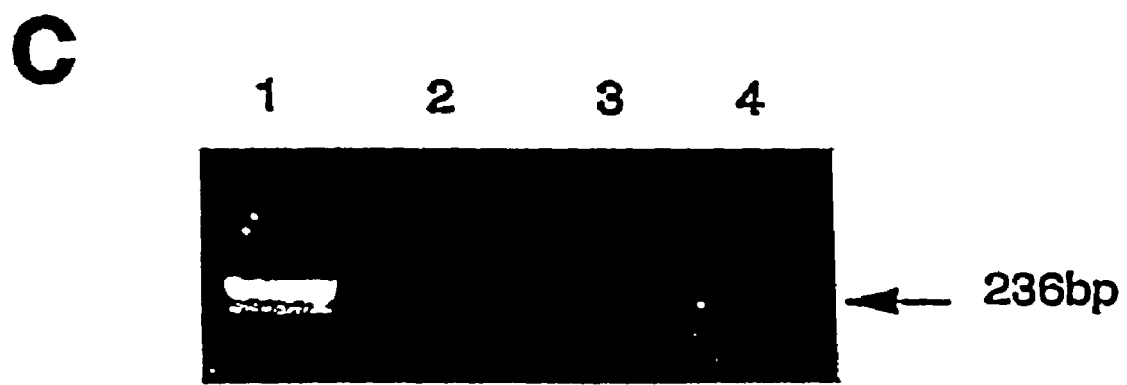

Since there had been no previous reports in the literature that cartilage cells, the chondrocytes, contain TnI, the cDNA encoding human cartilage TnI was cloned using a standard PCR strategy (Wu and Moses, 1996, *Gene* 18, 243-246) (FIG. 7A). Sequencing of the PCR product revealed its identity to human fast skeletal muscle TnI (FIG. 7B) (SEQ ID NO:16). TnI expression levels of rat xiphoid cartilage, Swarm rat chondrosarcoma and liver, were also determined by RT-PCR and were significantly lower than that of rat skeletal muscle, with the expression level in liver appearing to be slightly lower than that of cartilage or chondrosarcoma (FIG. 7C).

Figure 8:
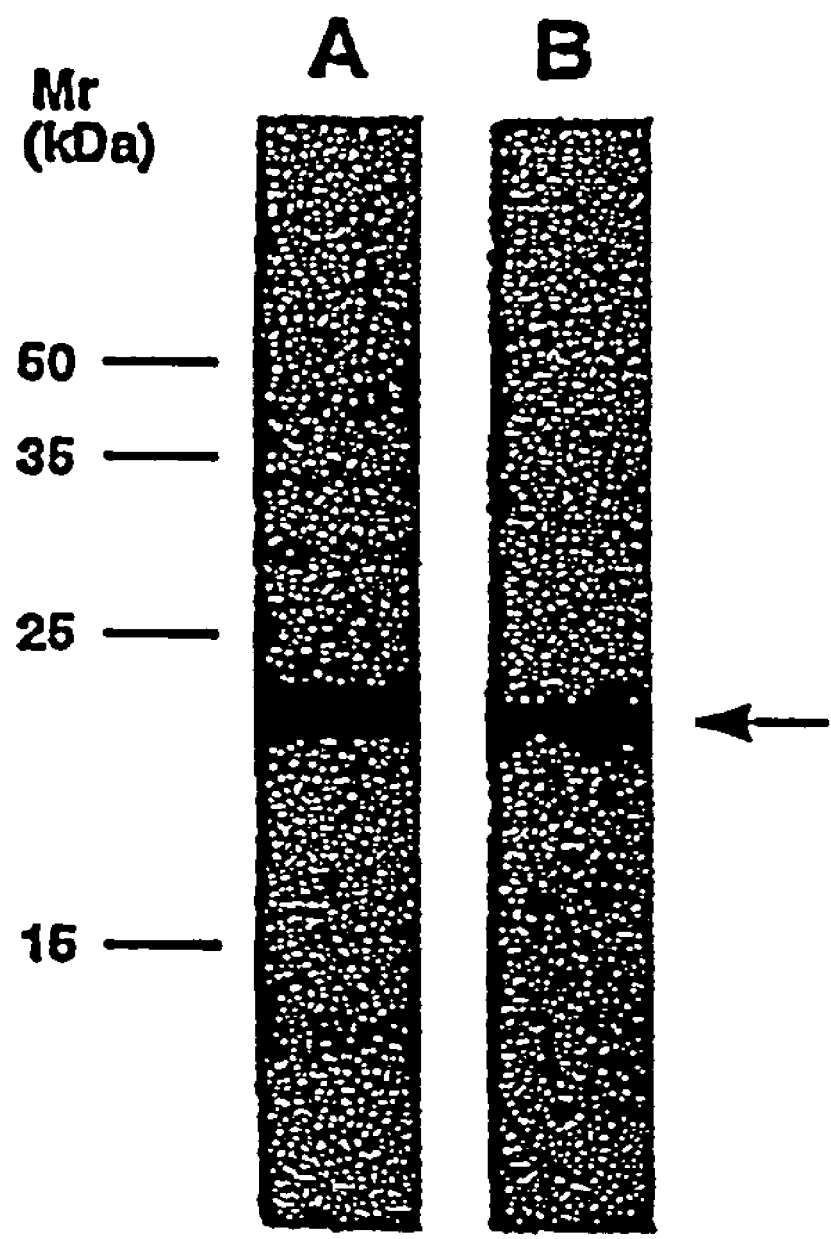

In order to obtain sufficient amounts of TnI to investigate its potential as an antiangiogenic factor, a cDNA encoding full length human fast skeletal muscle troponin I was cloned into expression vector pET-24d and transformed into *E. coli* BL21(DE3) p LysS strain. The expression level of recombinant human skeletal muscle troponin I was approximately 30-40% of total cellular protein. Following purification, recombinant TnI migrated as a single band, at approximately 21 kDa on SDS-PAGE (FIG. 8).

Example 8

Capillary Endothelial Cell (EC) Proliferation Cell Culture

Capillary EC, isolated from bovine adrenal cortex (Folkman, et al., 1979, *Proc. Natl. Acad. Sci. USA* 76, 5217-5221) were obtained from Children's Hospital (Boston, Mass.). These cells were demonstrated to be endothelial by staining with antisera to von Willebrand factor and by their uptake of fluoresceinated, acetylated low density lipoprotein. Cells were maintained in culture in DME (Dulbecco's Modified Eagle's Medium, Gibco Laboratories) with 10% calf serum (Hyclone) (DME/10) supplemented with 3 ng/ml bFGF or Vascular Endothelial Growth Factor (VEGF) in preparation for these assays.

BALB/c mouse 3T3 cells were maintained in DME/10, L-glutamine (292 μg/ml) as previously described (Klagsbrun, et al., 1977, *Exp. Cell Res.* 105, 99-108). Bovine aortic smooth muscle cells (SMC), isolated by explant from the medial layer of bovine aortas, were obtained from Children's Hospital (Boston, Mass.). These cells were cultured in DME/10 on uncoated tissue culture plastic as previously described (D'Amore and Smith, 1993, *Growth Factors* 8, 61-75).

Briefly, capillary EC (2,000 cells per well) were plated on gelatinized 96-Well culture plates in DMEM supplemented with 5% (v/v) calf serum and incubated for 24 hours. On day 2, cells were treated with bFGF (Scios Nova; 1 ng/ml) and challenged with the test fractions and/or with purified TnI. For experiments in which VEGF was used as the mitogen, 800 cells per well were plated and allowed to incubate for 3 hours before VEGF (Biomedical Technologies Incorporated; 30 ng/ml) and TnI was added. Control wells contained cells alone and cells stimulated with bFGF or VEGF. On day 5, growth medium was removed from the plates; cells were lysed in buffer containing the detergent Triton x-100 and the phosphatase substrate p-nitrophenyl phosphate. After incubation for 2 h at 37° C., NaOH was added to terminate the reaction. Color development was determined using a rapid multiwell plate reader (Dynatech MR 5000) (Moses, et al., 1990, *Science* 2488, 1408-1410; Moses, et al., 1990, *J. Cell. Biol.* 119, 474-481; Connolly, et al., 1986, *Anal. Biochem.* 152, 136-140). EC inhibitory activity was verified by electronic cell counting assays as previously described by us (Moses, et al., 1990, *Science* 2488, 1408-1410; Moses, et al., 1990, *J. Cell. Biol.* 119, 474-481). Tritiated thymidine incorporation assays were conducted according to the method of Shing (Shing, 1990, in *Methods in Enzymology*, eds. Barnes, D., Mather, J. P. and Sato, G. H. (Academic Press, New York), pp. 91-95).

Results

Figure 9A:
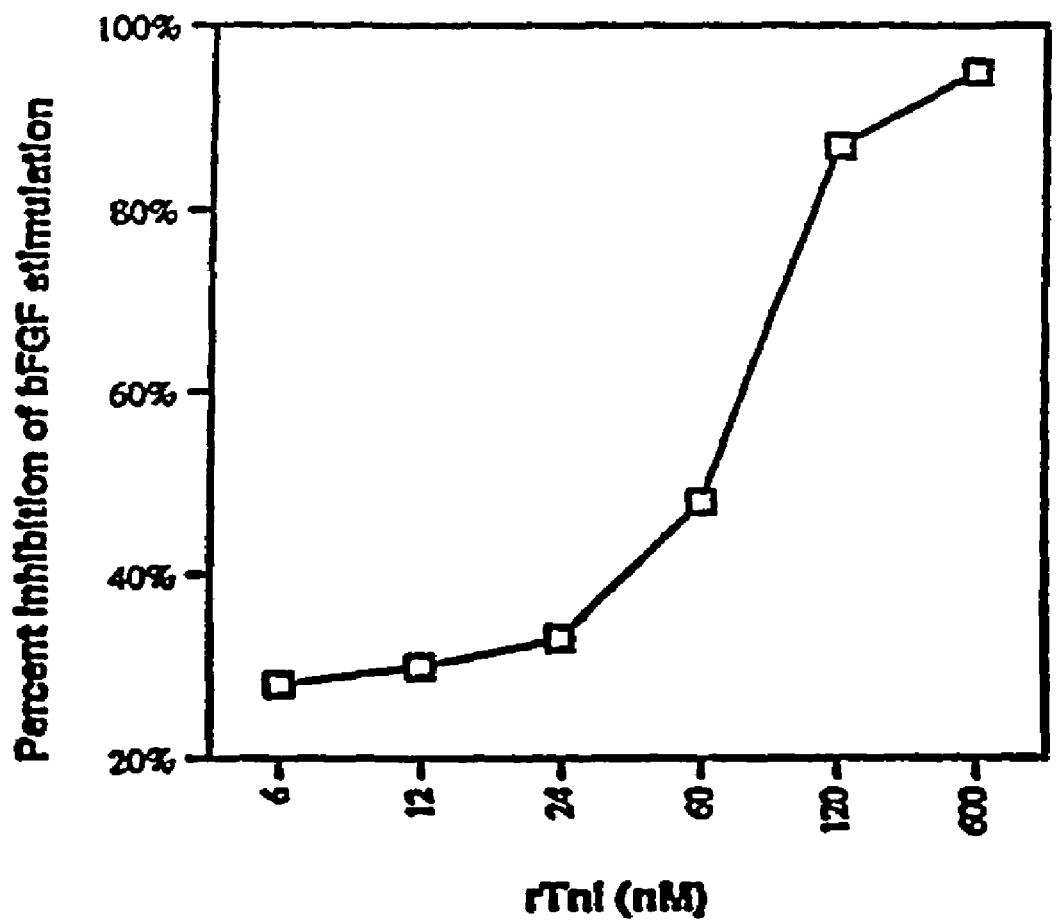
Figure 9B:
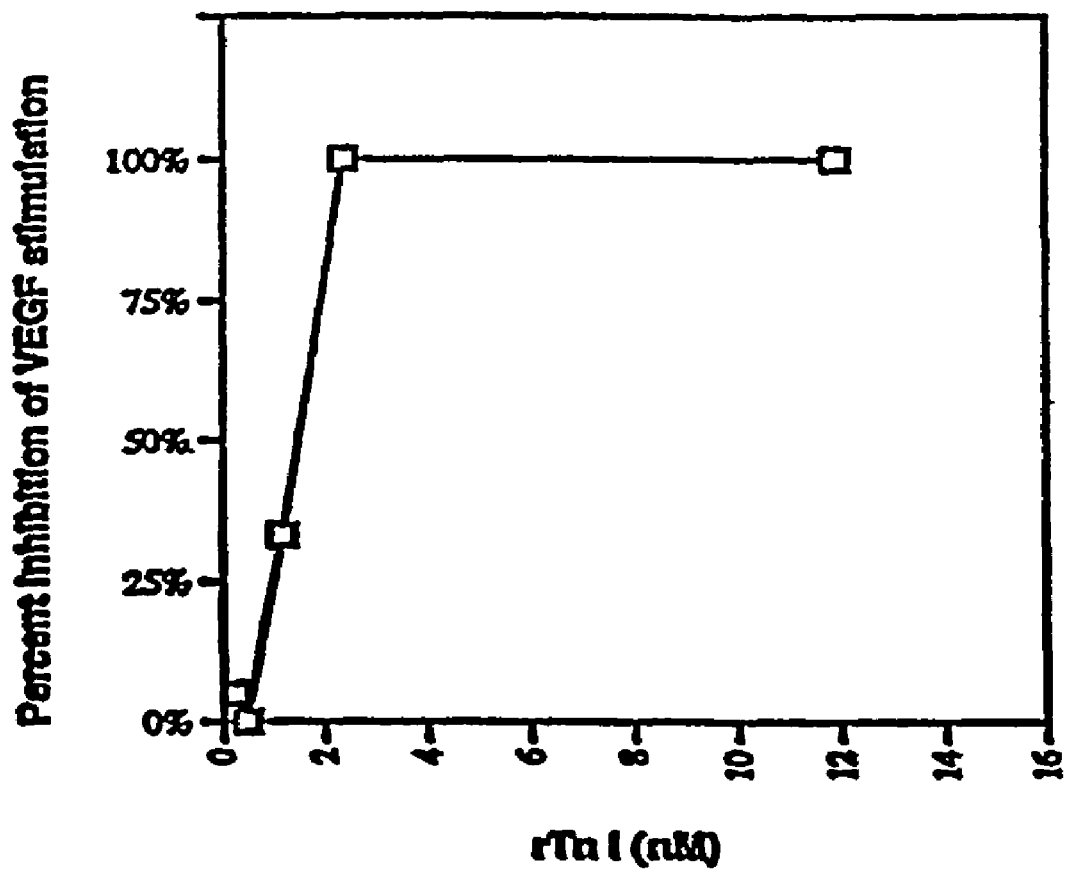

Purified rTnI was tested for its ability to inhibit bFGF and VEGF-stimulated capillary EC and was found to inhibit EC proliferation in a dose-dependent and saturable manner with an $IC_{50}$ (the inhibitory concentration at which one observes 50% suppression of proliferation) of approximately 65 nM when bFGF was used as the mitogen (FIG. 9A) and approximately 1.5 nM when VEGF was used (FIG. 9B). Native TnI inhibited capillary EC proliferation in an equipotent manner. Tritiated thymidine assays demonstrated that recombinant TnI inhibited capillary EC DNA synthesis in a dose-dependent and saturable manner with an $IC_{50}$ of approximately 240 nM. This suppression of proliferation appears to be unique to endothelial cells given the fact that TnI did not suppress the growth of any of the non-endothelial cells tested including bovine aortic smooth muscle cells and Balb/c 3T3 cells even when tested at doses which were over 5× higher than that required to obtain an $IC_{50}$ value for capillary EC.

Example 9

Cell Specificity

To determine whether the proliferation of bovine aortic SMC and Balb c/3T3 cells was inhibited by TnI, the following assays were conducted. SMC were plated into multiwell dishes (2.1 $cm^2$/well) at a density of 10,000 cells/well. After allowing the cells to attach overnight, fresh media was applied containing either 3 ng/ml PDGF-BB alone or in combination with increasing concentrations of purified TnI. Following incubation for 72 hrs at 37° C. in 10% $CO_2$, the cells were rinsed in PBS, detached by trypsinization and counted electronically. The effect of TnI on quiescent BALB/c mouse 3T3 cells was assessed by measuring the incorporation of tritiated thymidine into DNA in 96-well plates as previously described (Shing, 1990, in *Methods in Enzymology*, eds. Barnes, D., Mather, J. P. and Sato, G. H. (Academic Press, New York), pp. 91-95).

Example 10

Chick Chorioallantoic Membrane (CAM) Assay

All procedures were carried out in a laminar flow hood under sterile conditions. The eggs were stored in a Favorite Egg Incubator (Leahy) at 37° C. and 65% relative humidity. On day 3 of development, fertilized White Leghorn eggs (SPAFAS) were cracked and the embryos removed from their shells and placed in plastic petri dishes. On day 6, test substances including native rabbit TnI (Greaser and Gergely, 1971, *J. Biol. Chem.* 246, 4226-4233) and recombinant human TnI and appropriate buffer controls were mixed in methylcellulose, disks and applied to the surfaces of the growing CAMs above the dense subectodermal plexus. Forty-eight hours following implantation of the plastic disc, the eggs were examined for vascular reactions under a dissecting scope (60×) and photographed (Moses, et al., 1990, *Science* 2488, 1408-1410; Moses, et al., 1990, *J. Cell. Biol.* 119, 474-481).

Figure 10:
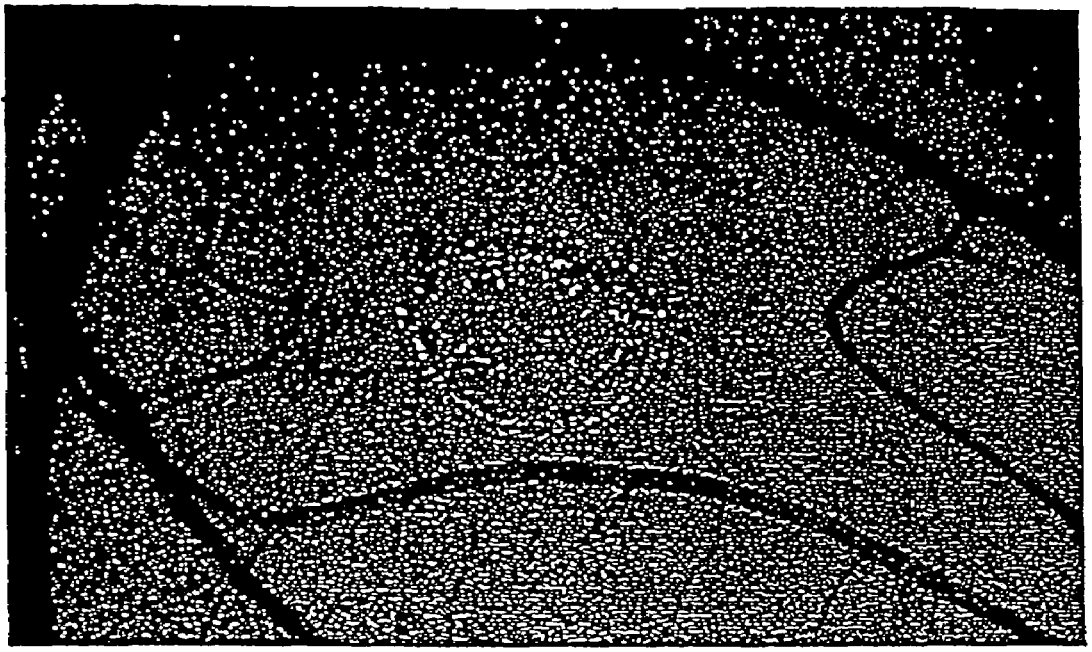
Figure 10:
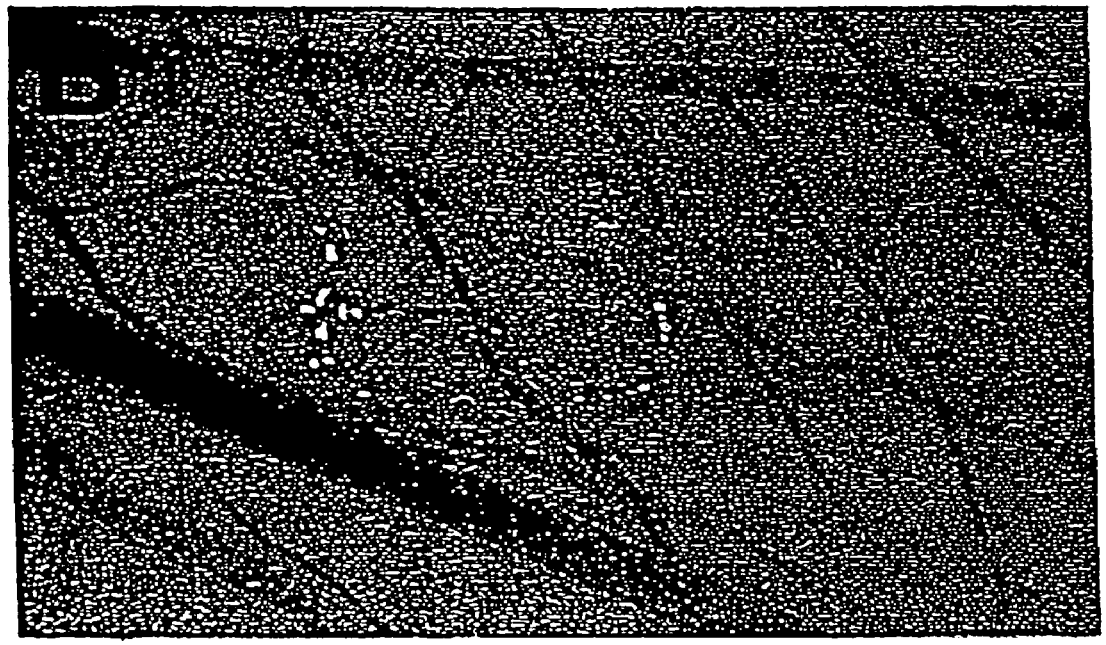

The CAM assay was used to determine whether rTnI was an inhibitor of angiogenesis in vivo. The results shown in FIG. 10 demonstrate the significant inhibition of embryonic neovascularization as evidenced by the large avascular zone caused by 130 picomoles of rTnI. This effect was observed in 66% of the eggs tested at this dose and 100% of the eggs tested at a dose of approximately 380 picomoles. This observation was reproduced in three separate sets of CAM assays using three different TnI preparations. Over 125 CAMs were tested in this series of experiments.

Example 11

Mouse Corneal Pocket Assay

Inhibition of angiogenesis in vivo was also demonstrated using the mouse corneal pocket assay (Chen, et al., 1995, *Cancer. Res.* 55, 4230-4233; O'Reilly, et al., 1996, *Nat. Med.* 2, 689-692). Briefly, pellets composed of bFGF (40 ng/ml), sucrose octasulfate and Hydron were implanted into corneal micropockets of six C57BL/6 mice as previously described (U.S. Pat. No. 5,837,680 to Moses et al.). Troponin I (50 mg/kg) was administered systemically every 12 hours by subcutaneous injection. On the sixth day of treatment, corneal angiogenesis was evaluated using slit lamp microscopy and photographed.

Results

Figure 11:
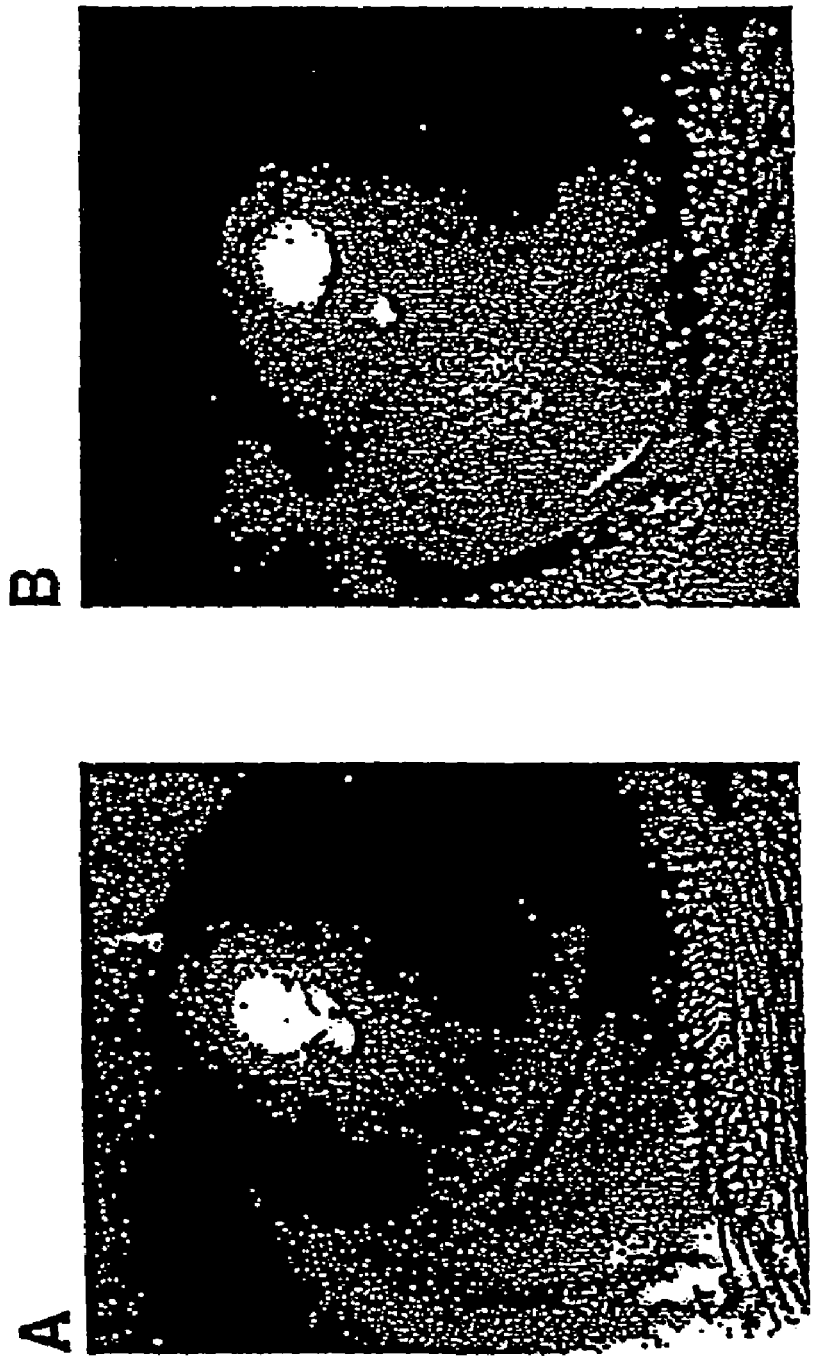

In another in vivo assay, the mouse corneal pocket assay, systemic administration of rTnI significantly inhibited bFGF-induced angiogenesis (FIG. 11B) when compared to corneas of control mice which received vehicle alone (FIG. 11A).

Taken together, the in vivo studies described in Section 6, Examples 10 and 11 show rTnI to be a potent inhibitor of neovascularization when compared to other inhibitors tested in these same assays (Moses, et al., 1995, in *International Review of Cytology*, 161, 1-48).

Example 12

B16-BL6 Melanoma Model

Murine melanoma B16-BL6 were cultured in RPMI 1640 (Gibco) supplemented with 10% (v/v) fetal calf serum (Hyclone), L-glutamine and NaHCO$_3$. Cells were washed with EBSS (Gibco) and trypsinized for 3 to 5 mm with 0.25% TRL/0.2% EDTA to which culture buffer was added for washing. This preparation was then centrifuged for 10 mm at 1000 rpm, the cell pellet resuspended in fresh culture media, cell number determined using a coulter counter and cell viability determined with trypan blue (100% viability). The cell suspension was adjusted to 2.5×10$^5$ cells/ml for implantation. B16-BL6 cells (5×10$^5$/0.2 ml) were injected into the tail veins of C57BL/6 mice (approximately 6-7 weeks old). One day following tumor cell inoculation, mice were treated with rTnI systemically, twice per week, with a dose of either 1 mg/kg (n=10) or 20 mg/kg (n=10) or vehicle (150 mM NaCl, 20 mM citrate, pH3) over, a 28 day period. On day 30, animals were sacrificed, the number of lung surface metastases counted and the lungs weighed.

Results

Recombinant TnI was tested for its ability to inhibit lung metastasis in vivo caused by a very aggressive variant of the B16 melanoma cell line, B16-BL6 (Saiki, et al., 1989 *Cancer Res.* 49, 3815-3822). Recombinant TnI, administered systemically, inhibited lung metastases by 52% ($p<0.04$ one tailed t-test) at a dose of 1 mg/kg when given only twice weekly (n=10), and by 64% ($p<0.02$; one tailed t-test) at a dose of 20 mg/kg twice weekly (n=10), [lung metastasis control (68.6+/−7.5 SEM) (n=10); 1 mg/kg (32.8+1−4.8 SEM); 20 mg/kg (25.0+/−7.5 SEM)] with no observed toxicity (i.e., no weight or appetite loss, etc.). Lung weights were comparable in control and treated groups.

As shown by the data, TnI inhibited lung metastasis.

Example 13

Inhibition of Endothelial Cell Proliferation Using Fragments of Troponin I

Figure 12:
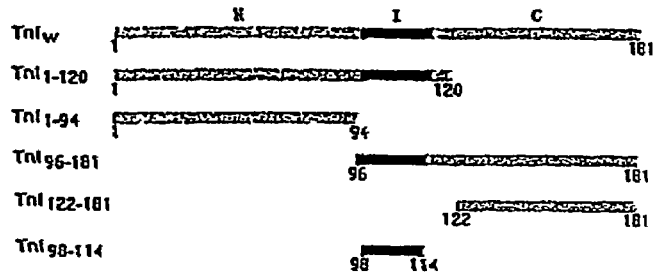

Recombinant peptides corresponding to fragments of rabbit (rb) TnI (SEQ ID NO:10) (FIG. 12) were tested for ability to inhibit bFGF-stimulated capillary EC as described above in Section 6, Examples 2 and 8. The rbTnI fragments (SEQ ID NOS:11-15) were prepared according to Jha et al., 1996, *Biochemistry* 35(34):11026-11035. As shown in Table 2, various concentrations of peptides corresponding to the amino-terminal (N') region (aa 1-94) (SEQ ID NO:11); the N' and inhibitory (I') region (aa 1-120) (SEQ ID NO:12); the I' region (aa 98-114) (SEQ ID NO:13); the carboxy terminus (C') and I' region (C'+I') (aa 96-181) (SEQ ID NO:14); the C' region (aa 122-181) (SEQ ID NO:15); and mixtures of the C'+I' (SEQ ID NO:14) plus the N' (SEQ ID NO:11) fragments and the N'+I' (SEQ ID NO:12) plus the C' (SEQ ID NO:15) fragments of TnI were tested for inhibition of EC proliferation.

As shown in Table 2, the C'+I' fragment (SEQ ID NO:14) significantly inhibited EC proliferation. The percent inhibition of EC was 54% and 48% at concentrations of 0.1 µg/well and 0.3 µg/well, respectively. The IC$_{50}$ was determined to be 0.1 to 0.2 µg/well (0.05 µM to 0.1 µM). Furthermore, the N'+I' (SEQ ID NO:12) fragment interfered with the inhibitory activity of the C' (SEQ ID NO:15) fragment and the N' (SEQ ID NO:11) fragment interfered with the inhibitory activity of the C'+I' (SEQ ID NO:14) fragment.

As shown in Section 6, Example 3, supra, full-length TnI inhibited EC proliferation approximately 46% at a concentration of 5 µg/well (1.2 µM). Thus, the C'+I' fragment had 25 to 50-fold EC inhibitory activity compared to the full-length TnI.

These results demonstrate that fragments of troponin subunits, particularly the C'+I' fragment (SEQ ID NO:14), inhibited EC proliferation in an assay that was developed to mimic the process of neovascularization. Thus, troponin subunit fragments inhibit angiogenesis.

TABLE 2

| SEQ ID NO: | Region[a] | Fragment | Amino Acids | Assay µg/well | Assay µg/ml | MW | Assay nM | % I[b] | Approx. IC$_{50}$ µg/well | Approx. IC$_{50}$ µM |
|---|---|---|---|---|---|---|---|---|---|---|
| 11 | 1-94 | N' | 94 | 0.01 | 0.05 | 10,906 | 5 | −12 | >0.3 | >0.1 |
|  |  |  |  | 0.025 | 0.125 |  | 11 | 6 |  |  |
|  |  |  |  | 0.1 | 0.5 |  | 46 | 31 |  |  |
|  |  |  |  | 0.3 | 1.5 |  | 138 | 28 |  |  |
| 12 | 1-120 | N' + I' | 120 | 0.01 | 0.05 | 13,923 | 4 | 6 | >>0.3 | >>0.1 |
|  |  |  |  | 0.025 | 0.025 |  | 9 | 0 |  |  |
|  |  |  |  | 0.1 | 0.5 |  | 36 | 12 |  |  |
|  |  |  |  | 0.3 | 1.5 |  | 108 | 17 |  |  |
| 13 | 98-114 | I' | 17 | 4 | 20 | 1,972 | 10140 | −12 | >>40 | >>100 |
|  |  |  |  | 10 | 50 |  | 25350 | −25 |  |  |
|  |  |  |  | 20 | 100 |  | 50700 | −6 |  |  |
|  |  |  |  | 40 | 200 |  | 101401 | −34 |  |  |
| 14 | 96-181 | C' + I' | 86 | 0.01 | 0.05 | 9,978 | 5 | 25 | 0.1 to 0.2 | 0.05 to 0.1 |
|  |  |  |  | 0.025 | 0.125 |  | 13 | 28 |  |  |
|  |  |  |  | 0.1 | 0.5 |  | 50 | 54 |  |  |
|  |  |  |  | 0.3 | 1.5 |  | 150 | 48 |  |  |
| 15 | 122-181 | C' | 60 | 0.01 | 0.05 | 6,961 | 7 | −1 | >0.3 | >0.2 |
|  |  |  |  | 0.025 | 0.125 |  | 18 | −6 |  |  |
|  |  |  |  | 0.1 | 0.5 |  | 72 | 20 |  |  |
|  |  |  |  | 0.3 | 1.5 |  | 215 | 23 |  |  |
| 14, 11 | 96-181 + 1-94 | (C' + I') + N' | 180 | 0.01 | 0.05 | 20,884 | 7 | 17 | >0.3 | >0.2 |
|  |  |  |  | 0.025 | 0.125 |  | 18 | 20 |  |  |
|  |  |  |  | 0.1 | 0.5 |  | 72 | 27 |  |  |
|  |  |  |  | 0.3 | 1.5 |  | 215 | 28 |  |  |

TABLE 2-continued

| SEQ ID NO: | Region[a] | Fragment | Amino Acids | Assay µg/well | Assay µg/ml | MW | Assay nM | % I[b] | Approx. IC$_{50}$ µg/well | Approx. IC$_{50}$ µM |
|---|---|---|---|---|---|---|---|---|---|---|
| 12, 15 | 1-120 + 122-181 | (N' + I') + C' | 180 | 0.01 | 0.05 | 20,884 | 7 | −7 | >>0.3 | >>0.2 |
| | | | | 0.025 | 0.125 | | 18 | −1 | | |
| | | | | 0.1 | 0.5 | | 72 | −6 | | |
| | | | | 0.3 | 1.5 | | 215 | −1 | | |
| | 94-113 | C' + I' | 20 | 20 | 100 | 2,500 | 40000 | 0 | >>20 | >>40 |
| | 98-117 | C' + I' | 20 | 20 | 100 | 2,500 | 40000 | 1 | >>20 | >>40 |
| | 102-121 | C' + I' | 20 | 20 | 100 | 2,500 | 40000 | 0 | >>20 | >>40 |
| | 106-125 | C' + I' | 20 | 20 | 100 | 2,500 | 40000 | 0 | >>20 | >>40 |
| | 110-129 | C' + I' | 20 | 20 | 100 | 2,500 | 40000 | 0 | >>20 | >>40 |
| | 114-133 | C' + I' | 20 | 20 | 100 | 2,500 | 40000 | 0 | >>20 | >>40 |
| | 118-137 | C' | 20 | 20 | 100 | 2,500 | 40000 | 37 | 40 | 80 |
| | | | | 40 | 200 | 2,500 | | 50 | | |
| | 116-123 | C' | 8 | 50 | 250 | 900 | 80000 | 9 | >>50 | >>278 |
| | 118-125 | C' | 8 | 50 | 250 | 900 | 278000 | 0 | >>50 | >>278 |
| | 120-127 | C' | 8 | 50 | 250 | 900 | 278000 | 10 | >>50 | >>278 |
| | 122-129 | C' | 8 | 50 | 250 | 900 | 278000 | 23 | >>50 | >>278 |
| | 124-131 | C' | 8 | 50 | 250 | 900 | 278000 | 16 | >>50 | >>278 |
| | 126-133 | C' | 8 | 50 | 250 | 900 | 278000 | 11 | >>50 | >>278 |
| | 128-135 | C' | 8 | 50 | 250 | 900 | 278000 | 29 | 150 | 834 |
| | 130-137 | C' | 8 | 50 | 250 | 900 | 278000 | 50 | 50 | 278 |
| | 132-139 | C' | 8 | 50 | 250 | 900 | 278000 | 43 | 75 | 417 |
| | 134-141 | C' | 8 | 50 | 250 | 900 | 278000 | 30 | 150 | 834 |
| | 136-143 | C' | 8 | 50 | 250 | 900 | 278000 | 0 | >>50 | >>278 |

[a]SEQ ID NO: 2 amino acid numbers
[b]Percent Inhibition

The invention claimed is:

1. An isolated peptide consisting of a region of troponin subunit I having amino acid residues 94-123 (huTnI 94-123) of SEQ ID NO:17.

2. A pharmaceutical composition comprising a peptide consisting of amino acid residues 94-123 (huTnI 94-123) of SEQ ID NO:17 and a pharmaceutically acceptable carrier.

3. The pharmaceutical composition of claim 2, in which the composition is formulated as a topical preparation.

4. The pharmaceutical composition of claim 2, in which the composition is formulated for intradermal administration.

5. The pharmaceutical composition of claim 2, in which the composition is formulated as a parenteral solution.

6. The pharmaceutical composition of claim 2, in which the composition is formulated for subcutaneous administration.

7. The pharmaceutical composition of claim 2, in which the composition is formulated for intranasal administration.

8. The pharmaceutical composition of claim 2, in which the composition is formulated for epidural administration.

9. The pharmaceutical composition of claim 2, in which the composition is formulated for ophthalmic administration.

10. The pharmaceutical composition of claim 2, in which the composition is formulated for oral administration and is in the form of tablets or capsules.

11. The pharmaceutical composition of claim 2, in which the composition is suitable for intraventricular injection.

12. The pharmaceutical composition of claim 2, in which the composition is suitable for intrathecal injection administration.

13. The pharmaceutical composition of claim 2, which is suitable for administration with an infusion pump.

14. The pharmaceutical composition of claim 2, in which the pharmaceutical composition is lyophilized.

15. The pharmaceutical composition of claim 2, in which the pharmaceutical composition is in liquid form.

16. The pharmaceutical composition of claim 15, in which the liquid comprises water.

17. The pharmaceutical composition of claim 15, in which the liquid comprises saline solution.

* * * * *

SEQUENCE LISTING

<160> NUMBER OF SEQ ID NOS: 20

<210> SEQ ID NO 1
<211> LENGTH: 160
<212> TYPE: PRT
<213> ORGANISM: Homo sapiens

<400> SEQUENCE: 1

Met Thr Asp Gln Gln Ala Glu Ala Arg Ser Tyr Leu Ser Glu Glu Met
 1               5                  10                  15

Ile Ala Glu Phe Lys Ala Ala Phe Asp Met Phe Asp Ala Asp Gly Gly
                20                  25                  30

Gly Asp Ile Ser Val Lys Glu Leu Gly Thr Val Met Arg Met Leu Gly
                35                  40                  45

Gln Thr Pro Thr Lys Glu Glu Leu Asp Ala Ile Ile Glu Glu Val Asp
        50                  55                  60

Glu Asp Gly Ser Gly Thr Ile Asp Phe Glu Glu Phe Leu Val Met Met
65                  70                  75                  80

Val Arg Gln Met Lys Glu Asp Ala Lys Gly Lys Ser Glu Glu Glu Leu
                85                  90                  95

Ala Glu Cys Phe Arg Ile Phe Asp Arg Asn Ala Asp Gly Tyr Ile Asp
                100                 105                 110

Pro Glu Glu Leu Ala Glu Ile Phe Arg Ala Ser Gly Glu His Val Thr
            115                 120                 125

Asp Glu Glu Ile Glu Ser Leu Met Lys Asp Gly Asp Lys Asn Asn Asp
        130                 135                 140

Gly Arg Ile Asp Phe Asp Glu Phe Leu Lys Met Met Glu Gly Val Gln
145                 150                 155                 160

<210> SEQ ID NO 2

<211> LENGTH: 182
<212> TYPE: PRT
<213> ORGANISM: Homo sapiens

<400> SEQUENCE: 2

Met Gly Asp Glu Glu Lys Arg Asn Arg Ala Ile Thr Ala Arg Arg Gln
1               5                   10                  15

His Leu Lys Ser Val Met Leu Gln Ile Ala Ala Thr Glu Leu Glu Lys
            20                  25                  30

Glu Glu Ser Arg Arg Glu Ala Glu Lys Gln Asn Tyr Leu Ala Glu His
        35                  40                  45

Cys Pro Leu His Ile Pro Gly Ser Met Ser Glu Val Gln Glu Leu
50                  55                  60

Cys Lys Gln Leu His Ala Lys Ile Asp Ala Ala Glu Glu Glu Lys Tyr
65                  70                  75                  80

Asp Met Glu Val Arg Val Gln Lys Thr Ser Lys Glu Leu Glu Asp Met
                85                  90                  95

Asn Gln Lys Leu Phe Asp Leu Arg Gly Lys Phe Lys Arg Pro Pro Leu
            100                 105                 110

Arg Arg Val Arg Met Ser Ala Asp Ala Met Leu Lys Ala Leu Leu Gly
        115                 120                 125

Ser Lys His Lys Val Cys Met Asp Leu Arg Ala Asn Leu Lys Gln Val
130                 135                 140

Lys Lys Glu Asp Thr Glu Lys Glu Arg Asp Leu Arg Asp Val Gly Asp
145                 150                 155                 160

Trp Arg Lys Asn Ile Glu Glu Lys Ser Gly Met Glu Gly Arg Lys Lys
                165                 170                 175

Met Phe Glu Ser Glu Ser
            180

<210> SEQ ID NO 3
<211> LENGTH: 258
<212> TYPE: PRT
<213> ORGANISM: Homo sapiens

<400> SEQUENCE: 3

Met Ser Asp Glu Glu Val Glu Gln Val Glu Glu Gln Tyr Glu Glu Glu
1               5                   10                  15

Glu Glu Ala Gln Glu Glu Glu Val Gln Asp Thr Ala Glu Glu
            20                  25                  30

Asp Ala Glu Glu Glu Lys Pro Arg Pro Lys Leu Thr Ala Pro Lys Ile
        35                  40                  45

Pro Glu Gly Glu Lys Val Asp Phe Asp Asp Ile Gln Lys Lys Arg Gln
50                  55                  60

Asn Lys Asp Leu Met Glu Leu Gln Ala Leu Ile Asp Ser His Phe Glu
65                  70                  75                  80

Ala Arg Lys Lys Glu Glu Glu Leu Val Ala Leu Lys Glu Arg Ile
                85                  90                  95

Glu Lys Arg Arg Ala Glu Arg Ala Glu Gln Gln Arg Ile Arg Ala Glu
            100                 105                 110

Lys Glu Arg Glu Arg Gln Asn Arg Leu Ala Glu Glu Lys Ala Arg Arg
        115                 120                 125

Glu Glu Glu Asp Ala Lys Arg Arg Ala Glu Asp Asp Leu Lys Lys Lys
130                 135                 140

Lys Ala Leu Ser Ser Met Gly Ala Asn Tyr Ser Ser Tyr Leu Ala Lys
145                 150                 155                 160

```
Ala Asp Gln Lys Arg Gly Lys Lys Gln Thr Ala Arg Glu Met Lys Lys
                165                 170                 175

Lys Ile Leu Ala Glu Arg Arg Lys Pro Leu Asn Ile Asp His Leu Gly
            180                 185                 190

Glu Asp Lys Leu Arg Asp Lys Ala Lys Glu Leu Trp Glu Thr Leu His
        195                 200                 205

Gln Leu Glu Ile Asp Lys Phe Glu Phe Gly Lys Leu Lys Arg Gln
    210                 215                 220

Lys Tyr Asp Ile Thr Thr Leu Arg Ser Arg Ile Asp Gln Ala Gln Lys
225                 230                 235                 240

His Ser Lys Lys Ala Gly Thr Pro Ala Lys Gly Lys Val Gly Gly Arg
                245                 250                 255

Trp Lys

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
gctctgcaaa cagctgcacg ccaag                                     25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
gcccagcagg gccttgagca tggca                                     25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
ctcaccatgg gagatgagga gaagc                                     25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 7
gcctcgagtg gcctaggact cggac                                     25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
```
gaacactgcc cgcctctgca catc                                                24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 9
gagcccagca gcgccttcag catg                                                24

<210> SEQ ID NO 10
<211> LENGTH: 181
<212> TYPE: PRT
<213> ORGANISM: Oryctolagus cuniculus

<400> SEQUENCE: 10

Gly Asp Glu Glu Lys Arg Asn Arg Ala Ile Thr Ala Arg Arg Gln His
1               5                   10                  15

Leu Lys Ser Val Met Leu Gln Ile Ala Ala Thr Glu Leu Glu Lys Glu
            20                  25                  30

Glu Gly Arg Arg Glu Ala Glu Lys Gln Asn Tyr Leu Ala Glu His Cys
        35                  40                  45

Pro Pro Leu Ser Leu Pro Gly Ser Met Ala Glu Val Gln Glu Leu Cys
    50                  55                  60

Lys Gln Leu His Ala Lys Ile Asp Ala Ala Glu Glu Glu Lys Tyr Asp
65                  70                  75                  80

Met Glu Ile Lys Val Gln Lys Ser Ser Lys Glu Leu Glu Asp Met Asn
                85                  90                  95

Gln Lys Leu Phe Asp Leu Arg Gly Lys Phe Lys Arg Pro Pro Leu Arg
            100                 105                 110

Arg Val Arg Met Ser Ala Asp Ala Met Leu Lys Ala Leu Leu Gly Ser
        115                 120                 125

Lys His Lys Val Cys Met Asp Leu Arg Ala Asn Leu Lys Gln Val Lys
    130                 135                 140

Lys Glu Asp Thr Glu Lys Glu Arg Asp Leu Arg Asp Val Gly Asp Trp
145                 150                 155                 160

Arg Lys Asn Ile Glu Glu Lys Ser Gly Met Glu Gly Arg Lys Lys Met
                165                 170                 175

Phe Glu Ser Glu Ser
            180

<210> SEQ ID NO 11
<211> LENGTH: 94
<212> TYPE: PRT
<213> ORGANISM: Oryctolagus cuniculus

<400> SEQUENCE: 11

Gly Asp Glu Glu Lys Arg Asn Arg Ala Ile Thr Ala Arg Arg Gln His
1               5                   10                  15

Leu Lys Ser Val Met Leu Gln Ile Ala Ala Thr Glu Leu Glu Lys Glu
            20                  25                  30

Glu Gly Arg Arg Glu Ala Glu Lys Gln Asn Tyr Leu Ala Glu His Cys
        35                  40                  45

Pro Pro Leu Ser Leu Pro Gly Ser Met Ala Glu Val Gln Glu Leu Cys
    50                  55                  60

Lys Gln Leu His Ala Lys Ile Asp Ala Ala Glu Glu Glu Lys Tyr Asp

```
                65                  70                  75                  80
Met Glu Ile Lys Val Gln Lys Ser Ser Lys Glu Leu Glu Asp
                    85                  90

<210> SEQ ID NO 12
<211> LENGTH: 120
<212> TYPE: PRT
<213> ORGANISM: Oryctolagus cuniculus

<400> SEQUENCE: 12

Gly Asp Glu Glu Lys Arg Asn Arg Ala Ile Thr Ala Arg Arg Gln His
 1               5                  10                  15

Leu Lys Ser Val Met Leu Gln Ile Ala Ala Thr Glu Leu Glu Lys Glu
                20                  25                  30

Glu Gly Arg Arg Glu Ala Glu Lys Gln Asn Tyr Leu Ala Glu His Cys
            35                  40                  45

Pro Pro Leu Ser Leu Pro Gly Ser Met Ala Glu Val Gln Glu Leu Cys
        50                  55                  60

Lys Gln Leu His Ala Lys Ile Asp Ala Ala Glu Glu Lys Tyr Asp
65                  70                  75                  80

Met Glu Ile Lys Val Gln Lys Ser Ser Lys Glu Leu Glu Asp Met Asn
                85                  90                  95

Gln Lys Leu Phe Asp Leu Arg Gly Lys Phe Lys Arg Pro Pro Leu Arg
            100                 105                 110

Arg Val Arg Met Ser Ala Asp Ala
        115                 120

<210> SEQ ID NO 13
<211> LENGTH: 18
<212> TYPE: PRT
<213> ORGANISM: Oryctolagus cuniculus

<400> SEQUENCE: 13

Lys Leu Phe Asp Leu Arg Gly Lys Phe Lys Arg Pro Pro Leu Arg Arg
 1               5                  10                  15

Val Arg

<210> SEQ ID NO 14
<211> LENGTH: 86
<212> TYPE: PRT
<213> ORGANISM: Oryctolagus cuniculus

<400> SEQUENCE: 14

Asn Gln Lys Leu Phe Asp Leu Arg Gly Lys Phe Lys Arg Pro Pro Leu
 1               5                  10                  15

Arg Arg Val Arg Met Ser Ala Asp Ala Met Leu Lys Ala Leu Leu Gly
                20                  25                  30

Ser Lys His Lys Val Cys Met Asp Leu Arg Ala Asn Leu Lys Gln Val
            35                  40                  45

Lys Lys Glu Asp Thr Glu Lys Glu Arg Asp Leu Arg Asp Val Gly Asp
        50                  55                  60

Trp Arg Lys Asn Ile Glu Glu Lys Ser Gly Met Glu Gly Arg Lys Lys
65                  70                  75                  80

Met Phe Glu Ser Glu Ser
                85

<210> SEQ ID NO 15
<211> LENGTH: 60
```

<212> TYPE: PRT
<213> ORGANISM: Oryctolagus cuniculus

<400> SEQUENCE: 15

```
Leu Lys Ala Leu Leu Gly Ser Lys His Lys Val Cys Met Asp Leu Arg
 1               5                  10                  15

Ala Asn Leu Lys Gln Val Lys Lys Glu Asp Thr Glu Lys Glu Arg Asp
            20                  25                  30

Leu Arg Asp Val Gly Asp Trp Arg Lys Asn Ile Glu Glu Lys Ser Gly
        35                  40                  45

Met Glu Gly Arg Lys Lys Met Phe Glu Ser Glu Ser
    50                  55                  60
```

<210> SEQ ID NO 16
<211> LENGTH: 196
<212> TYPE: DNA
<213> ORGANISM: Homo sapiens

<400> SEQUENCE: 16

```
gctctgcaaa cagctgcacg ccaagatcga tgcggctgaa gaggagaagt acgacatgga    60
ggtgagggtg cagaagacca gcaaggagct ggaggacatg aaccagaagc tatttgatct   120
gcgggccaag ttcaagcggc ccccactgcg gagggtgcgc atgtcggccg atgccatgct   180
caaggccctg ctgggc                                                    196
```

<210> SEQ ID NO 17
<211> LENGTH: 182
<212> TYPE: PRT
<213> ORGANISM: Homo sapiens

<400> SEQUENCE: 17

```
Met Gly Asp Glu Glu Lys Arg Asn Arg Ala Ile Thr Ala Arg Arg Gln
 1               5                  10                  15

His Leu Lys Ser Val Met Leu Gln Ile Ala Ala Thr Glu Leu Glu Lys
            20                  25                  30

Glu Glu Ser Arg Arg Glu Ala Glu Lys Gln Asn Tyr Leu Ala Glu His
        35                  40                  45

Cys Pro Pro Leu His Ile Pro Gly Ser Met Ser Glu Val Gln Glu Leu
    50                  55                  60

Cys Lys Gln Leu His Ala Lys Ile Asp Ala Ala Glu Glu Glu Lys Tyr
65                  70                  75                  80

Asp Met Glu Val Arg Val Gln Lys Thr Ser Lys Glu Leu Glu Asp Met
                85                  90                  95

Asn Gln Lys Leu Phe Asp Leu Arg Gly Lys Phe Lys Arg Pro Pro Leu
            100                 105                 110

Arg Arg Val Arg Met Ser Ala Asp Ala Met Leu Lys Ala Leu Leu Gly
        115                 120                 125

Ser Lys His Lys Val Cys Met Asp Leu Arg Ala Asn Leu Lys Gln Val
    130                 135                 140

Lys Lys Glu Asp Thr Glu Lys Glu Arg Asp Leu Arg Asp Val Gly Asp
145                 150                 155                 160

Trp Arg Lys Asn Ile Glu Glu Lys Ser Gly Met Glu Gly Arg Lys Lys
                165                 170                 175

Met Phe Glu Ser Glu Ser
            180
```

<210> SEQ ID NO 18

```
<211> LENGTH: 10
<212> TYPE: PRT
<213> ORGANISM: Artificial Sequence
<220> FEATURE:
<223> OTHER INFORMATION: Description of Artificial Sequence: tryptic
      peptide

<400> SEQUENCE: 18

Leu Gln Ile Ala Ala Thr Glu Leu Glu Lys
 1               5                  10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: tryptic
      peptide

<400> SEQUENCE: 19

Ile Asp Val Ala Glu Glu Glu Lys Tyr Asp Met Glu Val Lys
 1               5                  10

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: tryptic
      peptide

<400> SEQUENCE: 20

Leu Phe Asp Leu Arg
 1               5
```